(12) United States Patent
Smets et al.

(10) Patent No.: US 11,319,511 B2
(45) Date of Patent: May 3, 2022

(54) COMPOSITIONS COMPRISING ENCAPSULATES

(71) Applicant: The Procter & Gamble Company, Cincinnati, OH (US)

(72) Inventors: Johan Smets, Lubbeek (BE); Conny Erna Alice Joos, Buggenhout (BE); Pierre Verstraete, Woluwe St. Lambert (BE); Linsheng Feng, Menasha, WI (US); Fadi Selim Chakar, Neenah, WI (US); Robert Stanley Bobnock, Menasha, WI (US)

(73) Assignee: The Procter & Gamble Company, Cincinnati, OH (US)

( * ) Notice: Subject to any disclaimer, the term of this patent is extended or adjusted under 35 U.S.C. 154(b) by 121 days.

(21) Appl. No.: 16/703,896

(22) Filed: Dec. 5, 2019

(65) Prior Publication Data
US 2020/0181543 A1    Jun. 11, 2020

(30) Foreign Application Priority Data
Dec. 7, 2018    (EP) ..................... 18210908

(51) Int. Cl.
| | | |
|---|---|---|
| *C11D 3/37* | (2006.01) | |
| *C11D 3/50* | (2006.01) | |
| *A61K 8/11* | (2006.01) | |
| *A61Q 13/00* | (2006.01) | |
| *C11D 11/00* | (2006.01) | |

(52) U.S. Cl.
CPC ............ *C11D 3/505* (2013.01); *C11D 3/3765* (2013.01); *C11D 11/0017* (2013.01)

(58) Field of Classification Search
CPC ....... C11D 3/37; C11D 3/3765; C11D 3/3776; C11D 3/50; A61K 8/11; A61K 8/8129; A61K 8/8152; A61K 2800/412; A61K 2800/65; A61Q 13/00
See application file for complete search history.

(56) References Cited

U.S. PATENT DOCUMENTS

| | | | |
|---|---|---|---|
| 7,932,191 B2 | 4/2011 | Dungworth | |
| 8,784,984 B2 | 7/2014 | Grey | |
| 2006/0263518 A1 | 11/2006 | Schwantes | |
| 2011/0268802 A1 | 11/2011 | Dihora | |
| 2016/0304817 A1* | 10/2016 | Fernandez Prieto | .. C11D 3/505 |
| 2017/0002302 A1 | 1/2017 | Dihora | |
| 2018/0215982 A1* | 8/2018 | Zhang | ...................... B01J 13/02 |
| 2018/0265827 A1 | 9/2018 | Oh | |
| 2018/0289597 A1 | 10/2018 | Baxter | |
| 2018/0333341 A1 | 11/2018 | Nijakowski et al. | |
| 2018/0362892 A1* | 12/2018 | Beckholt | ................ C11D 3/505 |

FOREIGN PATENT DOCUMENTS

| | | |
|---|---|---|
| WO | WO2014189906 A2 | 11/2014 |
| WO | WO2018169531 A1 | 9/2018 |

OTHER PUBLICATIONS

Extended European Search Report; Application No. 18210908.2-1114; dated May 6, 2019; 9 pages.
PCT Search Report and Written Opinion for PCTUS2019/064569; dated Feb. 4, 2020; 12 pages.

* cited by examiner

*Primary Examiner* — Brian P Mruk
(74) *Attorney, Agent, or Firm* — Gregory S. Darley-Emerson

(57) ABSTRACT

Compositions that include encapsulates, the encapsulates having a core and a shell encapsulating the core, the shell including certain acrylate-based polymers. Processes for making and using such compositions.

21 Claims, No Drawings

COMPOSITIONS COMPRISING ENCAPSULATES

FIELD OF INVENTION

The present application relates to benefit-agent-containing encapsulates, compositions comprising such encapsulates, and processes for making and using such encapsulates and compositions.

BACKGROUND OF THE INVENTION

Benefit agents, such as perfumes, silicones, waxes, flavors, vitamins and fabric softening agents, are expensive and/or generally less effective when employed at high levels in consumer products, for example, personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost due to the agents' physical or chemical characteristics, or such agents may be incompatible with other compositional components or the situs that is treated. In an effort to improve such delivery efficiency, benefit agents have been encapsulated. The encapsulated benefit agents are core-shell encapsulates.

It is desired that encapsulated benefit agents, such as perfume encapsulates that have a shell that comprises a polyacrylate, provide benefits, such as perfume benefits, across several, many, or all consumer touch points. For example, it is desired that such capsules provide a perfume benefit to fabrics that are treated with such capsules when the fabrics are still wet from such treatment and after such fabrics have been dried. Unfortunately, encapsulated benefit agents leak benefit agent over time, possibly via diffusion in the finished product. Thus, the fabric odor is relatively reduced. If such leakage is minimized, for example, by increasing the encapsulate's shell strength, the fabric odor upon treatment may again be relatively reduced because not enough perfume is released from the capsules. This problem is particularly pronounced in fabric treatment products, such liquid fabric enhancers, liquid laundry detergents, unit dose laundry detergents and granule/powdered laundry detergents that comprise such encapsulates. Thus, what is needed is an encapsulate that exhibits decreased benefit agent leakage, yet which provides the desired odor profile—in particular an enhanced pre-rub benefit and a post-rub benefit to wet and dry fabrics.

One solution to providing core-shell encapsulates that have the desired shell strength/benefit agent release characteristics is to select monomers and oligomers that have right molecular weight and functionality. However, even when the right monomers and oligomers are selected, in the prior art a partitioning modifier is often employed. The partitioning modifier is provided to properly solubilize such monomers and oligomers so that the desired shell wall can be obtained. Unfortunately, the partitioning modifier takes up space in the finished encapsulate that could otherwise be filled with benefit agent active. In short, the partitioning modifier reduces the pay load of an encapsulate. Surprisingly, Applicants recognized that the partitioning modifier also keeps benefit agent actives, such as perfume, from plasticizing the encapsulate's shell wall. Thus, Applicants used such recognition to select monomers and oligomers that do not need as much or no solubility modification and, that when formed into a shell wall, are resistant to plasticization by benefit agent actives.

As a result, herein, Applicants disclose an encapsulate that has unexpectedly high pay load, yet which still exhibits decreased benefit agent leakage, and provides the desired odor profile—in particular an enhanced pre-rub benefit and a post-rub benefit to wet and dry fabrics and a process of making same. The encapsulates of the present disclosure may comprise a reduced amount of a partitioning modifier, or it may be that partitioning modifier is eliminated completely.

SUMMARY OF THE INVENTION

The present disclosure relates to compositions, particularly consumer products, that include encapsulates, the encapsulates having a core and a shell encapsulating the core, the shell including certain acrylate-based polymers. The present disclosure also relates to processes for making and using such compositions.

For example, the present disclosure relates to compositions that include a consumer product adjunct material and encapsulates having a volume weighted median encapsulate size from about 0.5 microns to about 100 microns, the encapsulates including a core and a shell; the shell encapsulating said core, the shell including a poly(meth)acrylate polymer including a reaction product of at least one monomer or oligomer thereof, the monomer including a structure according to formula I as described below; the core including a benefit agent and, based on total core weight, from greater than 0% to about 80% of a partitioning modifier; the composition being a consumer product.

The present disclosure also relates to a composition that includes a consumer product adjunct material and encapsulates, the encapsulates having a volume weighted median encapsulate size from about 0.5 microns to about 100 microns, the encapsulates including a core and a shell, the shell encapsulating said core; the shell including a poly(meth)acrylate polymer including a reaction product of at least a first monomer, a second monomer, and a third monomer, or oligomers thereof, the first monomer including the structure according to formula I as described below, the second monomer including a basic (meth)acrylate monomer, and the third monomer including an acidic (meth)acrylate monomer; and the core including a benefit agent; where the composition is a consumer product.

The present disclosure also relates to a method of treating a surface or an article, the method including contacting the surface or article with a composition as described herein, optionally in the presence of water.

DETAILED DESCRIPTION OF THE INVENTION

The present disclosure relates to encapsulates that include particular polymers in the walls of the encapsulates. The encapsulates may include partitioning modifiers in the core of the encapsulates. Without wishing to be bound by theory, it is believed that making the described choices in encapsulate design, for example with regard to monomer selection for the shell material, or partitioning modifier type and/or level, results in encapsulates that provide improved performance profiles.

In prior art systems, leakage tends to increase with increasing encapsulate size. A surprising aspect of presently described encapsulates is the unique combination of monomers, oligomers and/or prepolymers yielding a core-shell encapsulate as a benefit agent encapsulate wherein as the median encapsulate size of the benefit agent encapsulate increases, the one-week leakage decreases in a relative comparison to systems without the inventive combination.

It is generally known in the art that leakage typically increases as benefit agent encapsulates, such as core-shell encapsulates and microcapsules, increase in size. The present disclosure discloses relatively larger size core-shell encapsulates, for example greater than 20 um, that surprisingly achieve lower leakage relative to comparable sized encapsulates of the art.

The present disclosure relates to encapsulates that make possible achieving an unexpectedly high payload in the core, resulting in more efficient delivery of the benefit agent. The ratio, measured on the basis of weight of the benefit agent encapsulate, of core to shell may be greater than 2:1, or even 3:1, preferably 4:1 or even at least 10:1, or even at least 20:1. On a percentage basis by weight, the core as a percent of the benefit agent encapsulate may be at least 50%, or even from 60 to 98%, or in some aspects at least 75% or even at least 80%. Desirably the present disclosure relates to high payload encapsulates, such as 60 to 98%.

The resulting encapsulates of the present disclosure, for example with the partitioning modifier, are relatively large encapsulates, yet of lower leakage and of higher strength as compared to encapsulates known in in the art.

The encapsulates and related methods of the present disclosure are described in more detail below.

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrance (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the phrase "encapsulate" encompasses microcapsules, including perfume microcapsules. As used herein, the terms "encapsulate," "benefit agent containing delivery particle," "capsule," and "microcapsule" are synonymous and may be used interchangeably.

As used herein, reference to the term "(meth)acrylate" or "(meth)acrylic" is to be understood as referring to both the acrylate and the methacrylate versions of the specified monomer, oligomer and/or prepolymer. For example "allyl (meth)acrylate" indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible. Poly(meth)acrylate materials are intended to encompass a broad spectrum of polymeric materials including, for example, polyester poly(meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth)acrylate, ethylene glycol di(meth)acrylate, allyl (meth)acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth)acrylate, trimethylol propane tri(meth)acrylate, ethoxylated bisphenol A di(meth)acrylates, bisphenol A di(meth)acrylates, diglycerol di(meth)acrylate, tetraethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional (meth)acrylates. Monofunctional acrylates, i.e., those containing only one acrylate group, may also be advantageously used. Typical monoacrylates include 2-ethylhexyl (meth)acrylate, 2-hydroxyethyl (meth)acrylate, cyanoethyl (meth)acrylate, 2-hydroxypropyl (meth)acrylate, p-dimethylaminoethyl (meth)acrylate, lauryl (meth)acrylate, cyclohexyl (meth)acrylate, tetrahydrofurfuryl (meth)acrylate, chlorobenzyl (meth)acrylate, aminoalkyl(meth)acrylate, various alkyl(meth)acrylates and glycidyl (meth)acrylate.

Mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

For purposes of the present disclosure, propan-2-yl tetradecanoate is not considered a perfume raw material when calculating perfume compositions/formulations. Thus, the amount of propan-2-yl tetradecanoate present is not used to make such calculations.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Compositions

The present disclosure relates to compositions that include encapsulates and a consumer product adjunct material.

The composition may be a consumer product. The consumer product may be useful as a baby care, beauty care, fabric & home care, family care, feminine care, or health care product or device. The composition may be a beauty care composition, a fabric & home care composition, or combinations thereof.

The composition may be a beauty care composition, such as a hair treatment product (including shampoo and/or conditioner), a skin care product (including a cream, lotion, or other topically applied product for consumer use), a shave care product (including a shaving lotion, foam, or pre- or post-shave treatment), personal cleansing product (including a liquid body wash, a liquid hand soap, and/or a bar soap), a deodorant and/or antiperspirant, or mixtures thereof.

The composition may be a fabric treatment composition, such as a laundry detergent composition (including a heavy-duty washing detergent), a fabric conditioning composition (including a fabric softening and/or enhancing composition), a laundry and rinse additive, a fabric pre-treatment composition, a fabric refresher composition, or a mixture thereof.

The composition may be a home care composition, such as an air care, car care, dishwashing, hard surface cleaning and/or treatment, and other cleaning for consumer or institutional use.

The composition may be in any suitable form. For example, the composition may be in the form of a liquid composition, a granular composition, a single-compartment pouch, a multi-compartment pouch, a dissolvable sheet, a pastille or bead, a fibrous article, a tablet, a bar, a flake, a dryer sheet, or a mixture thereof. The composition can be selected from a liquid, solid, or combination thereof.

The composition may be in the form of a liquid. The liquid composition may include from about 30%, or from about 40%, or from about 50%, to about 99%, or to about 95%, or to about 90%, or to about 75%, or to about 70%, or to about 60%, by weight of the composition, of water. The liquid composition may be a liquid laundry detergent, a liquid fabric conditioner, a liquid dish detergent, a hair shampoo, a hair conditioner, or a mixture thereof.

The composition may be in the form of a solid. The solid composition may be a powdered or granular composition. Such compositions may be agglomerated or spray-dried. Such composition may include a plurality of granules or particles, at least some of which include comprise different compositions. The composition may be a powdered or granular cleaning composition, which may include a bleaching agent. The composition may be in the form of a bead or pastille, which may be pastilled from a liquid melt. The composition may be an extruded product.

The composition may be in the form of a unitized dose article, such as a tablet, a pouch, a sheet, or a fibrous article. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The composition may have a viscosity of from 1 to 1500 centipoises (1-1500 mPa*s), from 100 to 1000 centipoises (100-1000 mPa*s), or from 200 to 500 centipoises (200-500 mPa*s) at $20 \ s^{-1}$ and 21° C.

Additional components and/or features of the compositions, such as encapsulates and consumer product adjunct materials, are discussed in more detail below.

Encapsulates

The compositions and products of the present disclosure comprise encapsulates. The encapsulates typically comprise a core and a shell, where the shell encapsulates the core. As described in more detail below, the core may include a benefit agent and optionally a partitioning modifier, and the shell may comprise certain polymers.

The encapsulates may have a volume weighted median encapsulate size from about 0.5 microns to about 100 microns, or even 10 to 100 microns, preferably from about 1 micron to about 60 microns, or even 10 microns to 50 microns, or even 20 microns to 45 microns, or even 20 microns to 60 microns.

a. Shell

The encapsulates of the present disclosure include a shell. The shell may comprise certain polymers, which may be reaction products of certain monomers.

For example, the shells of the encapsulates described herein may comprise a poly(meth)acrylate polymer comprising a reaction product of at least one monomer or oligomer thereof. The monomer comprises a structure according to formula I

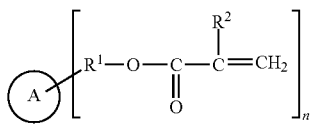

wherein $R^1$ is selected from $C_1$ to $C_8$, $R^2$ is hydrogen or methyl, wherein n is an integer from 1 to 3, and A is a ring structure selected from:

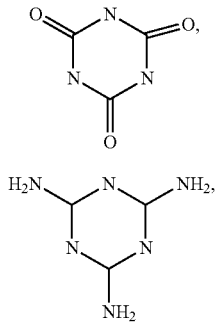

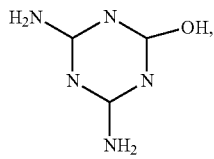

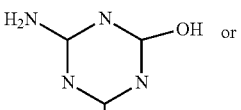

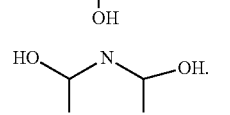

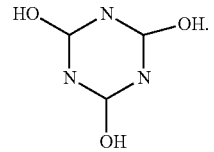

The core comprises a benefit agent. In addition, the encapsulate may comprise, based on total core weight, from about 0%, or from greater than 0%, to about 80%, or to about 50%, or to about 30%, or to about 20% of a partitioning modifier, described in more detail below. The encapsulate may comprise from about 0% to about 80%, or from greater than 0% to about 80%, or from greater than 0% to about 50%, or from greater than 0% to about 30%, or from greater than 0% to about 20%, by total core weight, of a partitioning modifier. The encapsulate may comprise no more than about 20%, by total core weight, of a partitioning modifier.

For ease of reference in this specification and in the claims, the term "monomer" or "monomers" as used herein is to be understood as monomers but also is inclusive of oligomers or monomers, and prepolymers formed of the specific monomers.

The present disclosure relates to a composition comprising a consumer product adjunct material and encapsulates, having a volume weighted median encapsulate size from about 0.5 microns to about 100 microns, preferably from about 1 micron to about 60 microns, said encapsulates comprising a core and a shell, said shell encapsulating said core, with the proviso that when A of formula I is structure II, said shell being free of polymers formed from monofunctional ethylenically unsaturated monomer. The shell may comprise a poly(meth)acrylate polymer, and the poly (meth)acrylate polymers may comprise a reaction product of at least three monomers or oligomers thereof. The first monomer may comprise a structure according to formula I

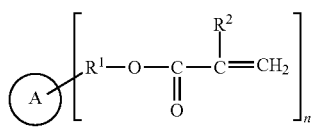

wherein $R^1$ is selected from $C_1$ to $C_8$ alkyl, $R^2$ is hydrogen or methyl, n is an integer from 1 to 3 and A is a ring structure selected from:

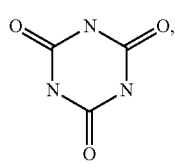

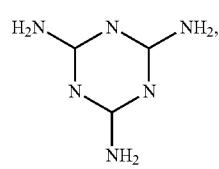

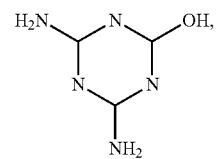

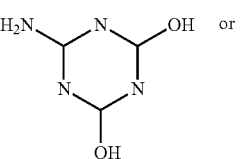

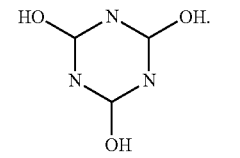

The second monomer, and/or oligomer or prepolymers thereof, may comprise a basic (meth)acrylate monomer and the third monomer may comprise an acidic (meth)acrylate monomer.

The basic (meth)acrylate monomer, and/or oligomer or prepolymers thereof, may comprise one or more of an amine modified methacrylate, amine modified acrylate, a monomer such as mono or diacrylate amine, mono or dimethacrylate amine, amine modified polyether acrylate, amine modified polyether methacrylate, aminoalkyl acrylate, or aminoalkyl methacrylate. The amines can be primary, secondary or tertiary amines. Preferably the alkyl moieties of the basic (meth)acrylate monomer are C1 to C12.

Suitable amine (meth)acrylates for use in the encapsulates of the present disclosure may include aminoalkyl acrylate or aminoalkyl methacrylate including, for example, but not by way of limitation, ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate, diethylamino acrylate, diethylamino methacrylate, diethylaminoethyl acrylate diethylaminoethyl methacrylate, dimethylaminoethyl acrylate and dimethylaminoethyl methacrylate. Preferably, the amine (meth)acrylate is aminoethyl acrylate or aminoethyl methacrylate, or tertiarybutyl aminoethyl methacrylate.

The acidic (meth)acrylate may comprise, by way of illustration, one or more of carboxy substituted acrylates or methacrylates, preferably carboxy substituted alkyl acrylates or methacrylates, such as carboxyalkyl acrylate, carboxyalkyl methacrylate, carboxyaryl acrylate, carboxy aryl methacrylate, and preferably the alky moieties are straight chain or branched C1 to C10. The carboxyl moiety can be bonded to any carbon of the C1 to C10 alkyl moiety, preferably a terminal carbon. Carboxy substituted aryl acrylates or methacrylates can also be used, or even (meth) acryloyloxyphenylalkylcarboxy acids. The alkyl moieties of the (meth)acryloyloxyphenylalkylcarboxy acids can be C1 to C10.

Suitable carboxy (meth)acrylates for use in encapsulates of the present disclosure may include 2-carboxyethyl acrylate, 2-carboxyethyl methacrylate, 2-carboxypropyl acrylate, 2-carboxypropyl methacrylate, carboxyoctyl acrylate, carboxyoctyl methacrylate. Carboxy substituted aryl acrylates or methacrylates may include 2-acryloyloxybenzoic acid, 3-acryloyloxybenzoic acid, 4-acryloyloxybenzoic acid, 2-methacryloyloxybenzoic acid, 3-methacryloyloxybenzoic acid, and 4-methacryloyloxybenzoic acid.

(Meth)acryloyloxyphenylalkylcarboxy acids by way of illustration and not limitation can include 4-acryloyloxyphenylacetic acid or 4-methacryloyloxyphenylacetic acid.

The basic (meth)acrylate monomer or oligomer may be present at less than 1% by weight of the encapsulate. The acidic (meth)acrylate monomer or oligomer may be present at less than 1% by weight of the encapsulate.

The described composition encapsulates may be characterized by a one-week leakage percent of the core of less than 25% by core weight, measured after storage for one week at 35° C.

In a useful embodiment, in formula I, n=3, $R^1$ is selected from $C_2$ to $C_5$ alkyl and A is

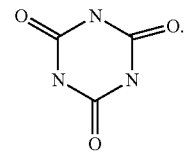

Monomers according to formula I can be selected from

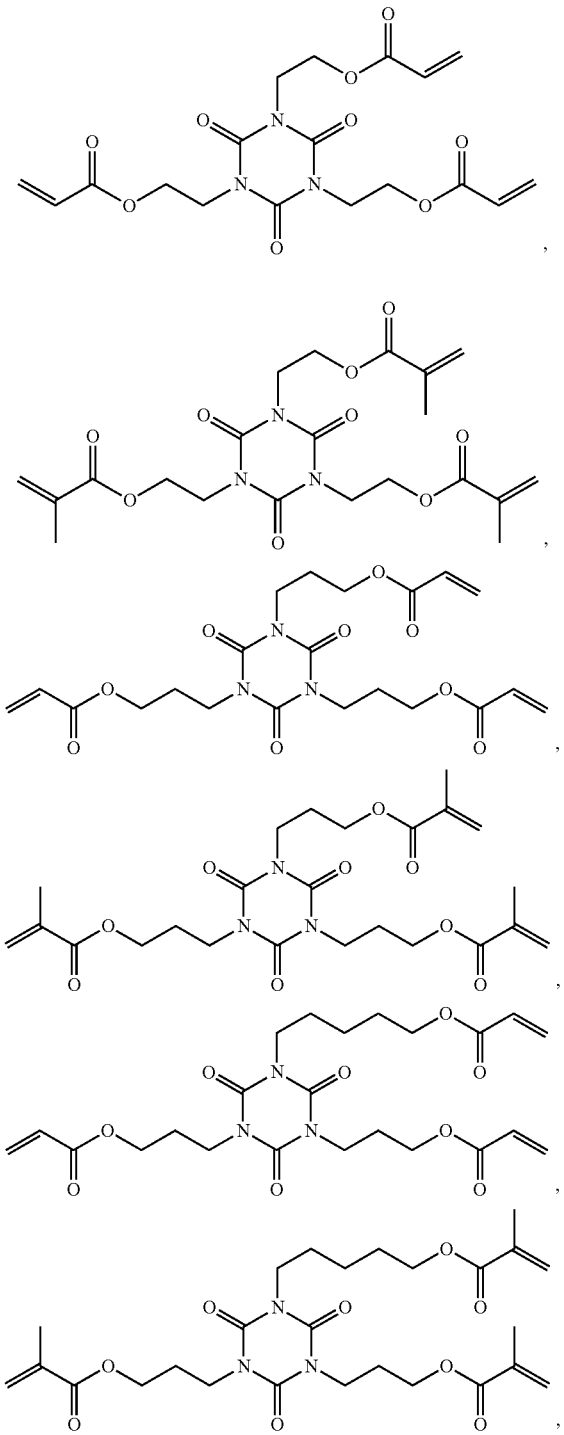

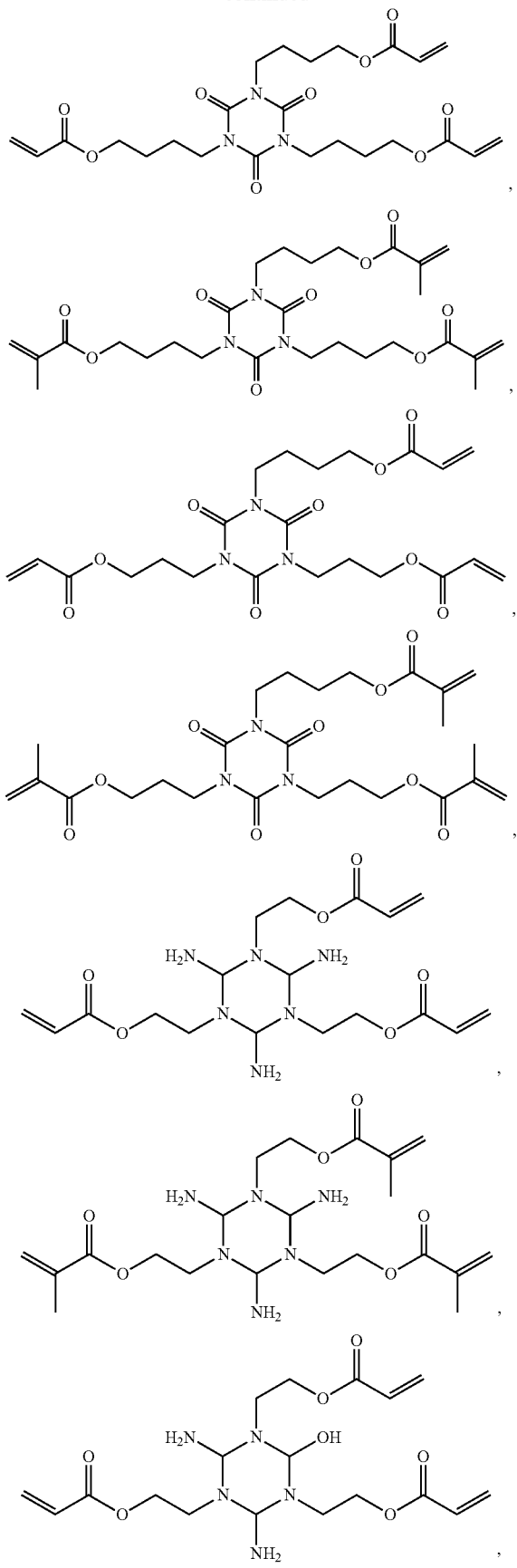

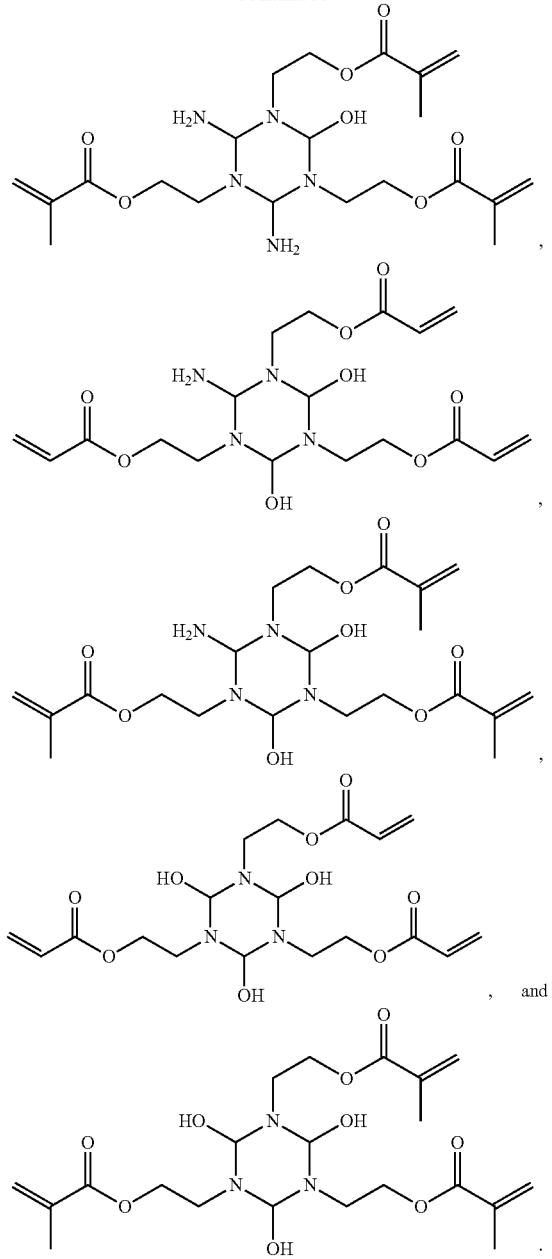

Optionally in the composition of the present disclosure, any of the first, second and third monomers may be oligomers, monomers or prepolymers.

The encapsulate, based on total encapsulate weight, may comprise from about 0.5% to about 40%, more preferably 0.8% to 5% of an emulsifier. Preferably the emulsifier is selected from the group consisting of polyvinyl alcohol, carboxylated or partially hydrolyzed polyvinyl alcohol, methyl cellulose, hydroxyethylcellulose, carboxymethylcellulose, methylhydroxypropylcellulose, salts or esters of stearic acid, lecithin, organosulphonic acid, 2-acrylamido-2-alkylsulphonic acid, styrene sulphonic acid, polyvinylpyrrolidone, copolymers of N-vinylpyrrolidone, polyacrylic acid, polymethacrylic acid; copolymers of acrylic acid and methacrylic acid, and water-soluble surfactant polymers which lower the surface tension of water. The emulsifier preferably comprises polyvinyl alcohol, and said polyvinyl alcohol preferably has a hydrolysis degree from about 55% to about 99%, preferably from about 75% to about 95%, more preferably from about 85% to about 90% and most preferably from about 87% to about 89%. The polyvinyl alcohol may have a viscosity of from about 40 cps to about 80 cps, preferably from about 45 cps to about 72 cps, more preferably from about 45 cps to about 60 cps and most preferably 45 cps to 55 cps in 4% water solution at 20° C. The polyvinyl alcohol may have a degree of polymerization of from about 1500 to about 2500, preferably from about 1600 to about 2200, more preferably from about 1600 to about 1900 and most preferably from about 1600 to about 1800. The weight average molecular weight of the polyvinyl alcohol may be of from about 130,000 to about 204,000 Daltons, preferably from about 146,000 to about 186,000, more preferably from about 146,000 to about 160,000, and most preferably from about 146,000 to about 155,000, and/or has a number average molecular weight of from about 65,000 to about 110,000 Daltons, preferably from about 70,000 to about 101,000, more preferably from about 70,000 to about 90,000 and most preferably from about 70,000 to about 80,000.

The encapsulates of the present disclosure may comprise a coating. The shell may comprise the coating; for example, the coating may be on an outer surface of the shell. The encapsulates may be manufactured and be subsequently coated with a coating material. The coating may be useful as a deposition aid. Non-limiting examples of coating materials include but are not limited to materials selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. The coating material may be a cationic polymer.

The compositions may comprise encapsulates according to the present disclosure wherein at least 75% of the encapsulates have an encapsulate wall (i.e., shell) thickness of from about 10 nm to about 350 nm, from about 20 nm to about 200 nm, or from 25 nm to about 180 nm, as determined by the Encapsulate Wall Thickness test method described herein.

b. Benefit Agent

The encapsulates of the present disclosure include a core that comprises a benefit agent. Suitable benefit agents located in the core may include benefit agents that provide benefits to a surface, such as a fabric or hair.

The benefit agent may be selected from the group consisting of perfume raw materials, silicone oils, waxes, hydrocarbons, higher fatty acids, essential oils, lubricants, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin care agents, glycerin, synthetic or natural actives, antibacterial actives, antiperspirant actives, cationic polymers, dyes and mixtures thereof.

The encapsulated benefit agent may include perfume raw materials. The term "perfume raw material" (or "PRM") as used herein refers to compounds having a molecular weight of at least about 100 g/mol and which are useful in imparting an odor, fragrance, essence or scent, either alone or with other perfume raw materials. Typical PRMs comprise inter alia alcohols, ketones, aldehydes, esters, ethers, nitrites and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

The PRMs may be characterized by their boiling points (B.P.) measured at the normal pressure (760 mm Hg), and their octanol/water partitioning coefficient (P), which may be described in terms of logP, determined according to the test method below. Based on these characteristics, the PRMs may be categorized as Quadrant I, Quadrant II, Quadrant III, or Quadrant IV perfumes, as described in more detail below.

The perfume raw materials may comprise a perfume raw material selected from the group consisting of perfume raw materials having a boiling point (B.P.) lower than about 250° C. and a ClogP lower than about 3, perfume raw materials having a B.P. of greater than about 250° C. and a ClogP of greater than about 3, perfume raw materials having a B.P. of greater than about 250° C. and a ClogP lower than about 3, perfume raw materials having a B.P. lower than about 250° C. and a ClogP greater than about 3 and mixtures thereof. Perfume raw materials having a boiling point B.P. lower than about 250° C. and a ClogP lower than about 3 are known as Quadrant I perfume raw materials. Quadrant 1 perfume raw materials are preferably limited to less than 30% of the perfume composition. Perfume raw materials having a B.P. of greater than about 250° C. and a ClogP of greater than about 3 are known as Quadrant IV perfume raw materials, perfume raw materials having a B.P. of greater than about 250° C. and a ClogP lower than about 3 are known as Quadrant II perfume raw materials, perfume raw materials having a B.P. lower than about 250° C. and a ClogP greater than about 3 are known as a Quadrant III perfume raw materials. Suitable Quadrant I, II, III and IV perfume raw materials are disclosed in U.S. Pat. No. 6,869,923 B1.

c. Partitioning Modifier

The core of the encapsulates of the present disclosure may comprise a partitioning modifier. The core may comprise, in addition to the encapsulated benefit agent, from greater than 0% to about 80%, preferably from greater than 0% to about 50%, more preferably from greater than 0% to about 30%, most preferably from greater than 0% to about 20%, based on total core weight, of a partitioning modifier.

The partitioning modifier may comprise a material selected from the group consisting of vegetable oil, modified vegetable oil, mono-, di-, and tri-esters of $C_4$-$C_{24}$ fatty acids, isopropyl myristate, dodecanophenone, lauryl laurate, methyl behenate, methyl laurate, methyl palmitate, methyl stearate, and mixtures thereof. The partitioning modifier may preferably comprise or consist of isopropyl myristate. The modified vegetable oil may be esterified and/or brominated. The modified vegetable oil may preferably comprise castor oil and/or soy bean oil. US Patent Application Publication 20110268802, incorporated herein by reference, describes other partitioning modifiers that may be useful in the presently described benefit agent encapsulates.

d. Method of Making Encapsulates

The encapsulates of the present disclosure may be made according to any known method using suitable starting materials. For example, encapsulates may be made by a process that comprises heating, in one or more heating steps, an emulsion, the emulsion produced by emulsifying the combination of: (a) a first composition formed by combining a first oil and a second oil, said first oil comprising a perfume, an initiator, and a partitioning modifier, preferably a partitioning modifier that comprises a material selected from the group consisting of vegetable oil (preferably comprising castor oil and/or soy bean oil), modified vegetable oil (preferably esterified and/or brominated), propan-2-yl tetradecanoate (i.e., isopropyl myristate) and mixtures thereof; preferably said partitioning modifier comprises propan-2-yl tetradecanoate; said second oil comprising (i) an oil soluble aminoalkylacylate and/or methacrylate monomer; (ii) a carboxy alkyl acrylate monomer and/or oligomer; (iii) a material selected from the group consisting of a multifunctional acrylate monomer, multifunctional methacrylate monomer, multifunctional methacrylate oligomer, multifunctional acrylate oligomer and mixtures thereof; (iv) a perfume; and (b) a second composition comprising water, a pH adjuster, an emulsifier, preferably an anionic emulsifier, preferably said emulsifier comprises polyvinyl alcohol and optionally an initiator.

In the described process, the heating step comprises heating the emulsion from about 1 hour to about 20 hours, preferably from about 2 hours to about 15 hours, more preferably about 4 hours to about 10 hours, most preferably from about 5 to about 7 hours, and/or heating sufficiently to transfer from about 500 joules/kg to about 5000 joules/kg, or from about 1000 joules/kg to about 4500 joules/kg, or from about 2900 joules/kg to about 4000 joules/kg to the emulsion.

The emulsion may be characterized by, prior to said heating step, a volume weighted median encapsulate size from about 0.5 microns to about 100 microns, preferably from about 1 microns to about 60 microns, more preferably from about 10 microns to about 25 microns or from about 0.5 microns to about 10 microns.

The weight ratio of the first composition to the second composition may be from about 1:9 to about 1:1, preferably from about 3:7 to about 4:6. The weight ratio of the first oil to the second oil may be from about 99:1 to about 1:99, preferably 9:1 to about 1:9, more preferably 6:4 to about 8:2.

A slurry can be made by combining encapsulates made by the above process. One or more perfumes that are different from the perfume or perfumes contained in the core of the encapsulates can be used external to the core-shell encapsulates.

Consumer Product Adjunct Material

The compositions of the present disclosure, which may be consumer products, may comprise a consumer product adjunct material. The consumer product adjunct material may provide a benefit in the intended end-use of a composition, or it may be a processing and/or stability aid.

Suitable consumer product adjunct materials may include: surfactants, conditioning actives, deposition aids, rheology modifiers or structurants, bleach systems, stabilizers, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, silicones, hueing agents, aesthetic dyes, additional perfumes and perfume delivery systems, structure elasticizing agents, carriers, hydrotropes, processing aids, structurants, anti-agglomeration agents, coatings, formaldehyde scavengers, and/or pigments.

Depending on the intended form, formulation, and/or end-use, compositions of the present disclosure or may not may not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments.

The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

a. Surfactants

The compositions of the present disclosure may comprise surfactant. Surfactants may be useful for providing, for example, cleaning benefits. The compositions may comprise a surfactant system, which may contain one or more surfactants.

The compositions of the present disclosure may include from about 1% to about 70%, or from about 2% to about 60%, or from about 5% to about 50%, by weight of the composition, of a surfactant system. Liquid compositions may include from about 5% to about 40%, by weight of the composition, of a surfactant system. Compact formulations, including compact liquids, gels, and/or compositions suitable for a unit dose form, may include from about 25% to about 70%, or from about 30% to about 50%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES), alkyl sulfates (AS), or mixtures thereof. Other suitable anionic surfactants include branched modified alkyl benzene sulfonates (MLAS), methyl ester sulfonates (MES), sodium lauryl sulfate (SLS), sodium lauryl ether sulfate (SLES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine).

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branhed alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

Depending on the formulation and/or the intended end-use, the composition may be substantially free of certain surfactants. For example, liquid fabric enhancer compositions, such as fabric softeners, may be substantially free of anionic surfactant, as such surfactants may negatively interact with cationic ingredients.

b. Conditioning Active

The compositions of the present disclosure may include a conditioning active. Compositions that contain conditioning actives may provide softness, anti-wrinkle, anti-static, conditioning, anti-stretch, color, and/or appearance benefits.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof.

The composition may include a quaternary ammonium ester compound, a silicone, or combinations thereof, preferably a combination. The combined total amount of quaternary ammonium ester compound and silicone may be from about 5% to about 70%, or from about 6% to about 50%, or from about 7% to about 40%, or from about 10% to about 30%, or from about 15% to about 25%, by weight of the composition. The composition may include a quaternary ammonium ester compound and silicone in a weight ratio of from about 1:10 to about 10:1, or from about 1:5 to about 5:1, or from about 1:3 to about 1:3, or from about 1:2 to about 2:1, or about 1:1.5 to about 1.5:1, or about 1:1.

The composition may contain mixtures of different types of conditioning actives. The compositions of the present disclosure may contain a certain conditioning active but be substantially free of others. For example, the composition may be free of quaternary ammonium ester compounds, silicones, or both. The composition may comprise quaternary ammonium ester compounds but be substantially free of silicone. The composition may comprise silicone but be substantially free of quaternary ammonium ester compounds.

c. Deposition Aid

The compositions of the present disclosure may comprise a deposition aid. Deposition aids can facilitate deposition of encapsulates, conditioning actives, perfumes, or combinations thereof, improving the performance benefits of the compositions and/or allowing for more efficient formulation of such benefit agents. The composition may comprise, by weight of the composition, from 0.0001% to 3%, preferably from 0.0005% to 2%, more preferably from 0.001% to 1%, or from about 0.01% to about 0.5%, or from about 0.05% to about 0.3%, of a deposition aid. The deposition aid may be a cationic or amphoteric polymer, preferably a cationic polymer.

Cationic polymers in general and their methods of manufacture are known in the literature. Suitable cationic polymers may include quaternary ammonium polymers known the "Polyquaternium" polymers, as designated by the International Nomenclature for Cosmetic Ingredients, such as Polyquaternium-6 (poly(diallyldimethylammonium chloride), Polyquaternium-7 (copolymer of acrylamide and diallyldimethylammonium chloride), Polyquaternium-10 (quaternized hydroxyethyl cellulose), Polyquaternium-22 (copolymer of acrylic acid and diallyldimethylammonium chloride), and the like.

The deposition aid may be selected from the group consisting of polyvinylformamide, partially hydroxylated polyvinylformamide, polyvinylamine, polyethylene imine, ethoxylated polyethylene imine, polyvinylalcohol, polyacrylates, and combinations thereof. The cationic polymer may comprise a cationic acrylate.

Deposition aids can be added concomitantly with encapsulates (at the same time with, e.g., encapsulated benefit agents) or directly/independently in the fabric treatment composition. The weight-average molecular weight of the polymer may be from 500 to 5000000 or from 1000 to 2000000 or from 2500 to 1500000 Dalton, as determined by size exclusion chromatography relative to polyethyleneoxide standards using Refractive Index (RI) detection. The weight-average molecular weight of the cationic polymer may be from 5000 to 37500 Dalton.

d. Rheology Modifier/Structurant

The compositions of the present disclosure may contain a rheology modifier and/or a structurant. Rheology modifiers may be used to "thicken" or "thin" liquid compositions to a desired viscosity. Structurants may be used to facilitate phase stability and/or to suspend or inhibit aggregation of particles in liquid composition, such as the encapsulates as described herein.

Suitable rheology modifiers and/or structurants may include non-polymeric crystalline hydroxyl functional structurants (including those based on hydrogenated castor oil), polymeric structuring agents, cellulosic fibers (for example, microfibrillated cellulose, which may be derived from a bacterial, fungal, or plant origin, including from wood), di-amido gellants, or combinations thereof.

Polymeric structuring agents may be naturally derived or synthetic in origin. Naturally derived polymeric structurants may comprise hydroxyethyl cellulose, hydrophobically modified hydroxyethyl cellulose, carboxymethyl cellulose, polysaccharide derivatives and mixtures thereof. Polysaccharide derivatives may comprise pectine, alginate, arabinogalactan (gum Arabic), carrageenan, gellan gum, xanthan gum, guar gum and mixtures thereof. Synthetic polymeric structurants may comprise polycarboxylates, polyacrylates, hydrophobically modified ethoxylated urethanes, hydrophobically modified non-ionic polyols and mixtures thereof. Polycarboxylate polymers may comprise a polyacrylate, polymethacrylate or mixtures thereof. Polyacrylates may comprise a copolymer of unsaturated mono- or di-carbonic acid and $C_1$-$C_{30}$ alkyl ester of the (meth)acrylic acid. Such copolymers are available from Noveon inc under the tradename Carbopol Aqua 30. Another suitable structurant is sold under the tradename Rheovis CDE, available from BASF.

Process of Making a Composition

The present disclosure relates to processes for making any of the compositions described herein. The process of making a composition, which may be a consumer product, may comprise the step of combining an encapsulate as described herein with a consumer product adjunct material as described herein.

The encapsulates may be combined with such one or more consumer product adjuncts materials when the encapsulates are in one or more forms, including a slurry form, neat encapsulate form, and/or spray dried encapsulate form. The encapsulates may be combined with such consumer product adjuncts materials by methods that include mixing and/or spraying.

The compositions of the present disclosure can be formulated into any suitable form and prepared by any process chosen by the formulator. The encapsulates and adjunct materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders.

Method of Treating a Surface or Article

The present disclosure further relates to methods of treating a surface or article with a composition according to the present disclosure. Such methods may provide cleaning, conditioning, and/or freshening benefits.

Suitable surfaces or articles may include fabrics (including clothing, towels, or linens), hard surfaces (such as tile, porcelain, linoleum or wood floors), dishware, hair, skin, or mixtures thereof.

The method may include a step of contacting a surface or article with a composition of the present disclosure. The composition may be in neat form or diluted in a liquor, for example, a wash or rinse liquor. The composition may be diluted in water prior, during, or after contacting the surface or article. The surface or article may be optionally washed and/or rinsed before and/or after the contacting step.

The method of treating and/or cleaning a surface or article may include the steps of:
 a) optionally washing, rinsing and/or drying the surface or article;
 b) contacting the surface or article with a composition as described herein, optionally in the presence of water;
 c) optionally washing and/or rinsing the surface or article; and
 d) optionally dried by drying passively and/or via an active method such as a laundry dryer.

For purposes of the present invention, washing includes but is not limited to, scrubbing, and mechanical agitation. The fabric may comprise most any fabric capable of being laundered or treated in normal consumer use conditions.

Liquors that may comprise the disclosed compositions may have a pH of from about 3 to about 11.5. When diluted, such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

The present disclosure further relates to a surface or article treated with a composition as described herein. The surface or article treated with a composition according to the present disclosure may comprise encapsulates according to the present disclosure, for example in or on a surface following treatment.

Combinations

Specifically contemplated combinations of the disclosure are herein described in the following lettered paragraphs. These combinations are intended to be illustrative in nature and are not intended to be limiting.

A. A composition comprising a consumer product adjunct material and encapsulates having a volume weighted median encapsulate size from about 0.5 microns to about 100 microns, preferably from about 1 micron to about 60 microns, said encapsulates comprising a core and a shell, said shell encapsulating said core, (a) said shell comprising a poly(meth)acrylate polymer comprising a reaction product of at least one monomer or oligomer thereof, (i) the monomer comprising a structure according to formula I

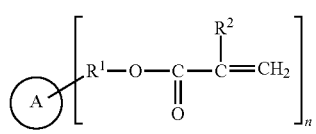

wherein $R^1$ is selected from $C_1$ to $C_8$ alkyl; wherein $R^2$ is hydrogen or methyl; wherein n is an integer from 1 to 3; wherein A is a ring structure selected from:

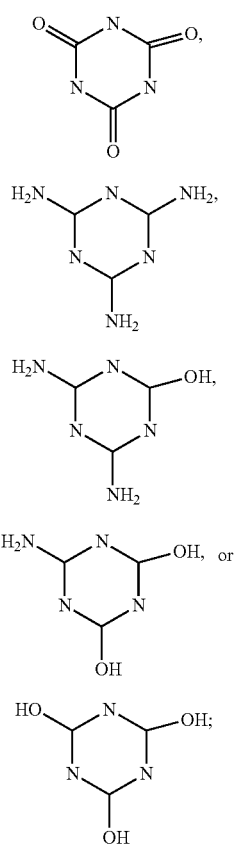

(b) said core comprising a benefit agent; said core further comprising, based on total core weight, from greater than 0% to about 80%, preferably from greater than 0% to 50%, more preferably from greater than 0% to about 30%, most preferably from greater than 0% to about 20% of a partitioning modifier, said composition being a consumer product.

B. The composition according to claim 1, wherein said poly(meth)acrylate polymer of the shell comprises a reaction product of at least three monomers or oligomers thereof comprising a first monomer, a second monomer, and a third monomer, (a) the first monomer comprising the structure according to formula I, (b) the second monomer comprising a basic (meth)acrylate monomer, and (c) the third monomer comprising an acidic (meth)acrylate monomer.

C. A composition comprising a consumer product adjunct material and encapsulates, said encapsulates having a volume weighted median encapsulate size from about 0.5 microns to about 100 microns, preferably from about 1 micron to about 60 microns, said encapsulates comprising a core and a shell, said shell encapsulating said core, (a) said shell comprising a poly(meth)acrylate polymer comprising a reaction product of at least a first monomer, a second monomer, and a third monomer, or oligomers thereof, (i) the first monomer comprising the structure according to formula I in paragraph A, wherein $R^1$ is selected from $C_1$ to $C_8$ alkyl; wherein $R^2$ is hydrogen or methyl; wherein n is an integer from 1 to 3; wherein A is a ring structure selected from any one of formulas II, III, IV, V, or VI in paragraph A; with the proviso that when A of formula I is structure II, said shell being free of polymers formed from monofunctional ethylenically unsaturated monomer; (ii) the second monomer comprising a basic (meth)acrylate monomer, (iii) the third monomer comprising an acidic (meth)acrylate monomer; and (b) said core comprising a benefit agent; wherein said composition is a consumer product.

D. The composition according to claim 3, wherein said core further comprises, a partitioning modifier, preferably, based on total core weight, from greater than 0% to about 80%, more preferably from greater than 0% to 50%, even more preferably from greater than 0% to about 30%, and even more preferably from greater than 0% to about 20% of a partitioning modifier.

E. The composition according to any preceding claim wherein the volume weighted median encapsulate size is from 25 microns to 60 microns.

F. The composition according to any preceding claim, wherein said encapsulates have a one-week leakage percent of the core of less than 25% by weight, measured after storage for one week at 35° C.

G. The composition according to any preceding claim, wherein the basic (meth)acrylate monomer or oligomer thereof comprises less than 1% by weight of the encapsulate and the acidic (meth)acrylate monomer or oligomer thereof comprises less than 1% by weight of the encapsulate.

H. The composition according to any preceding claim, wherein in formula I, n=3, $R^1$ is selected from $C_2$ to $C_5$ alkyl and A is

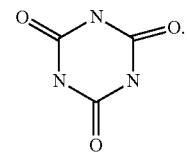

I. The composition according to any preceding claim, wherein the monomer according to formula I is selected from

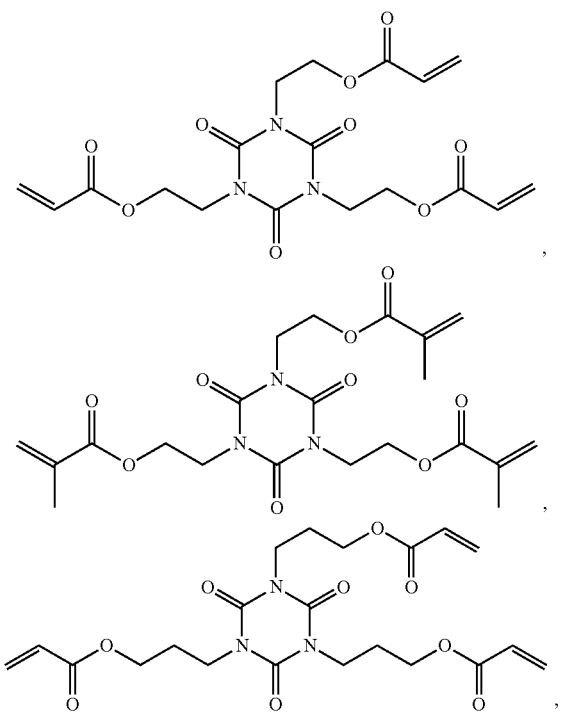

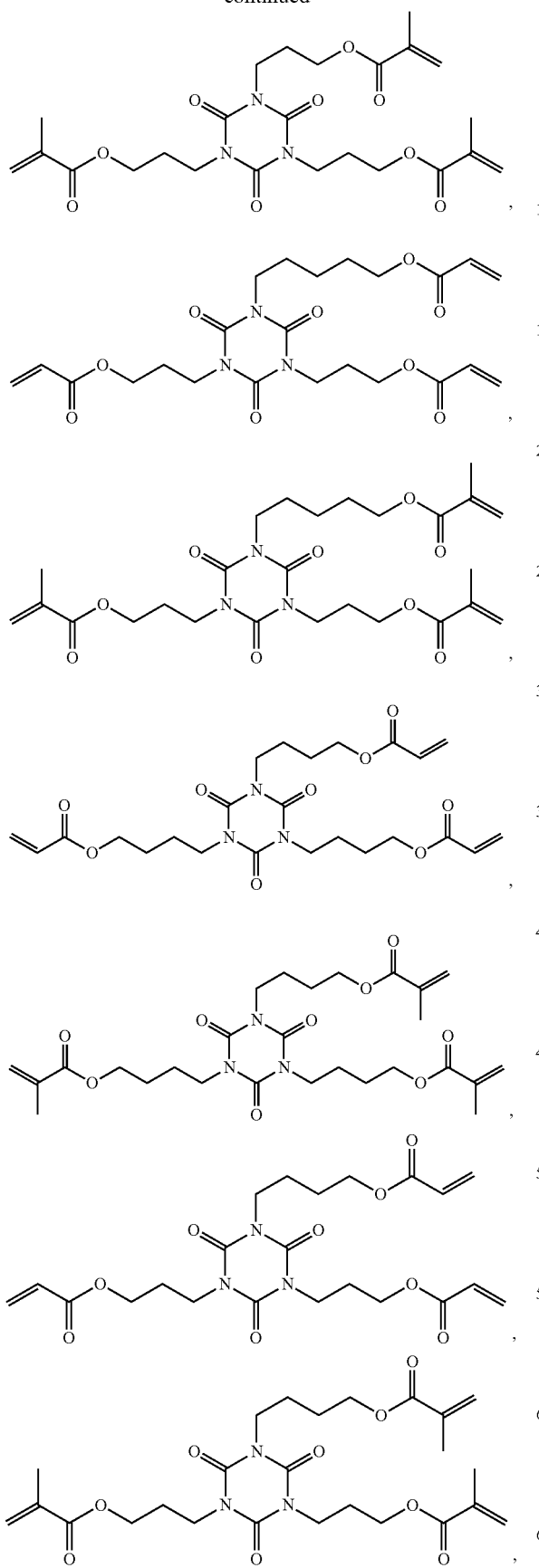
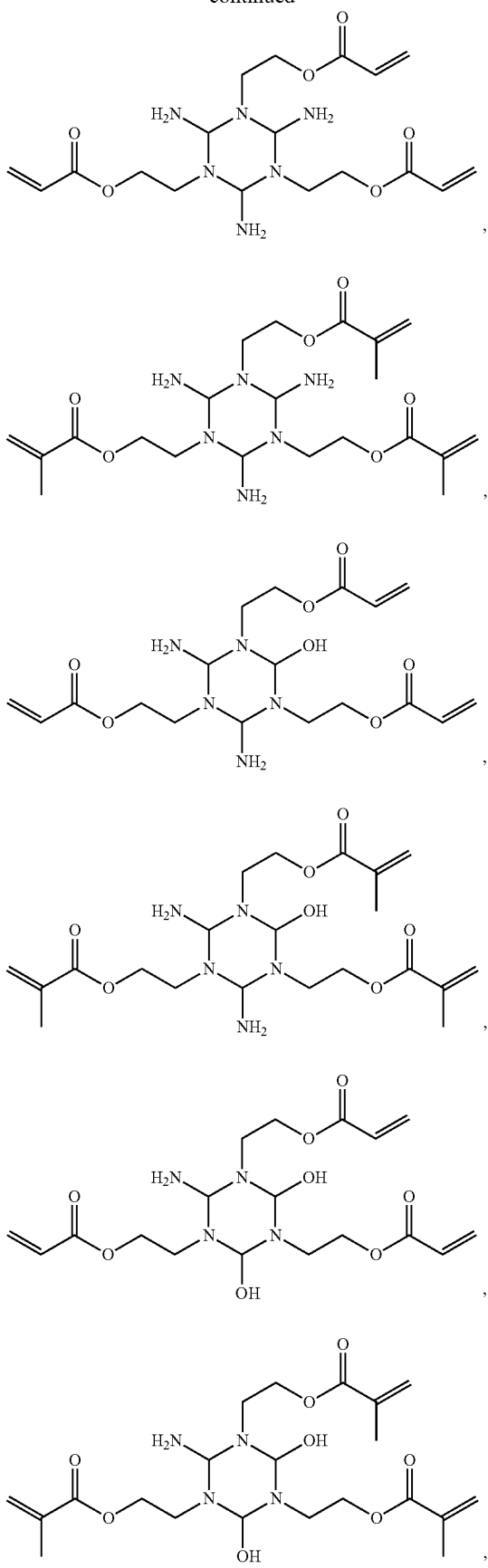

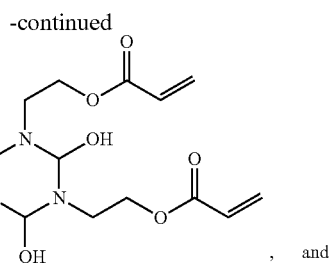

, and

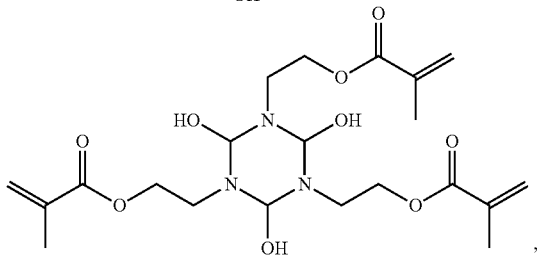

, or an oligomer of any such monomer.

J. The composition according to any preceding claim, wherein said partitioning modifier comprising a modifier selected from the group consisting of vegetable oil, modified vegetable oil, mono-, di-, and tri-esters of $C_4$-$C_{24}$ fatty acids, propan-2-yl tetradecanoate (i.e., isopropyl myristate), dodecanophenone, lauryl laurate, methyl behenate, methyl laurate, methyl palmitate, methyl stearate, and mixtures thereof, preferably isopropyl myristate.

K. The composition according to any preceding claim, wherein the encapsulate, based on total encapsulate weight, comprises from about 0.5% to about 40%, more preferably 0.8% to 5% of an emulsifier, preferably said emulsifier is selected from the group consisting of polyvinyl alcohol, carboxylated or partially hydrolyzed polyvinyl alcohol, methyl cellulose, hydroxyethylcellulose, carboxymethylcellulose, methylhydroxypropylcellulose, salts or esters of stearic acid, lecithin, organosulphonic acid, 2-acrylamido-2-alkylsulphonic acid, styrene sulphonic acid, polyvinylpyrrolidone, copolymers of N-vinylpyrrolidone, polyacrylic acid, polymethacrylic acid, copolymers of acrylic acid and methacrylic acid, and water-soluble surfactant polymers which lower the surface tension of water, more preferably said emulsifier comprises polyvinyl alcohol, preferably said polyvinyl alcohol has at least one of the following properties:
  (i) a hydrolysis degree from about 55% to about 99%, preferably from about 75% to about 95%, more preferably from about 85% to about 90%, most preferably from about 87% to about 89%; and/or
  (ii) a viscosity of from about 40 cps to about 80 cps, preferably from about 45 cps to about 72 cps, more preferably from about 45 cps to about 60 cps, most preferably 45 cps to 55 cps in 4% water solution at 20° C.; and/or
  (iii) a degree of polymerization of from about 1500 to about 2500, preferably from about 1600 to about 2200, more preferably from about 1600 to about 1900, most preferably from about 1600 to about 1800; and/or
  (iv) a weight average molecular weight of from about 130,000 to about 204,000 Daltons, preferably from about 146,000 to about 186,000, more preferably from about 146,000 to about 160,000, most preferably from about 146,000 to about 155,000; and/or
  (v) a number average molecular weight of from about 65,000 to about 110,000 Daltons, preferably from about 70,000 to about 101,000, more preferably from about 70,000 to about 90,000, most preferably from about 70,000 to about 80,000.

L. The composition according to any preceding claim, wherein any of the first, second and third monomers are oligomers or prepolymers of the monomers.

M. The composition according to any preceding claim, wherein the basic (meth)acrylate monomer or oligomer comprises an aminoalkyl acrylate or aminoalkyl methacrylate, wherein the alkyl moieties are from one to twelve carbons.

N. The composition according to any preceding claim, wherein the basic (meth)acrylate monomer is selected from the group consisting of ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate, diethylamino acrylate, diethylamino methacrylate, diethylaminoethyl acrylate diethylaminoethyl methacrylate, dimethylaminoethyl acrylate and dimethylaminoethyl methacrylate.

O. The composition according to any preceding claim, wherein the acidic (meth)acrylate monomer or oligomer comprises a carboxy-substituted acrylate or methacrylate monomer.

P. The composition according to any preceding claim, wherein the acidic (meth)acrylate monomer comprises a carboxyalkyl acrylate, carboxyalkyl methacrylate, carboxyaryl acrylate, carboxy aryl methacrylate, or (meth)acryloyloxyphenylalkylcarboxy acid, wherein the alky moieties are from one to twelve carbons.

Q. The composition according to any preceding claim, wherein the acidic (meth)acrylate monomer is selected from the group consisting of 2-carboxyethyl acrylate, 2-carboxyethyl methacrylate, 2-carboxypropyl acrylate, 2-carboxypropyl methacrylate, carboxyoctyl acrylate, carboxyoctyl methacrylate, 2-acryloyloxybenzoic acid, 3-acryloyloxybenzoic acid, 4-acryloyloxybenzoic acid, 2-methacryloyloxybenzoic acid, 3-methacryloyloxybenzoic acid, and 4-methacryloyloxybenzoic acid, 4-acryloyloxyphenylacetic acid, and 4-methacryloyloxyphenylacetic acid.

R. The composition according to any preceding claim, wherein the encapsulate comprises a coating on said shell, preferably said coating comprises a coating material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines, copolymers of polyvinyl amines, polyvinyl formamides, polyallyl amines, and mixtures thereof.

S. The composition according to any preceding claim, wherein said consumer product adjunct material comprises, based on total composition weight, from about 0.1% to about 50%, preferably from about 1% to about 35%, more preferably from about 2% to about 25%, more preferably from about 3% to about 20%, more preferably from about 5% to about 15%, most preferably from about 8% to about 12% or from about 3% to about 12%, preferably from about 4% to about 10%, more preferably from about 5% to about 8% of a conditioning active, preferably said conditioning active is selected from the group consisting of quaternary ammonium compounds, amines, fatty esters, sucrose esters, silicones, dispersible polyolefins, clays, polysaccharides, fatty acids, softening oils, polymer latexes and mixtures thereof.

T. A composition according to any preceding claim, wherein said consumer product adjunct material comprises from about 1% to about 70%, or from about 2% to about 60%, or from about 5% to about 50%, by weight of the composition, of a surfactant system.

U. A composition according to any preceding claim, wherein said benefit agent is selected from the group consisting of perfume raw materials, lubricants, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin care agents, synthetic or natural actives, antibacterial actives, antiperspirant actives, cationic polymers, dyes, and mixtures thereof, preferably perfume raw materials.

V. The composition according to any preceding claim, said consumer product adjunct material is selected from the group consisting of: surfactants, conditioning actives, deposition aids, rheology modifiers or structurants, bleach systems, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, additional perfumes and perfume delivery systems, structure elasticizing agents, carriers, hydrotropes, processing aids, structurants, anti-agglomeration agents, coatings, formaldehyde scavengers, pigments, and mixtures thereof, preferably at least a structurant, a deposition aid, or a mixture thereof.

W. A composition according to any preceding claim, wherein at least 75% of said encapsulates have a diameter of greater than 15 micrometers, preferably greater than 20 micrometers, more preferably greater than 25 micrometers, determined according to the Encapsulate Size (Diameter) test method described herein.

X. A composition according to any preceding claim, wherein at least 75% of said encapsulates have an encapsulate wall thickness of from about 10 nm to about 350 nm, from about 20 nm to about 200 nm, or from 25 nm to about 180 nm, as determined by the Encapsulate Wall Thickness test method disclosed herein.

Y. A composition according to any preceding claim, having a viscosity of from 1 to 1500 centipoises (1-1500 mPa*s), or from 100 to 1000 centipoises (100-1000 mPa*s), or from 200 to 500 centipoises (200-500 mPa*s) at 20 s$^{-1}$ and 21° C.

Z. A composition according to any preceding claim, comprising from about 0.001% to about 25%, based on total consumer product mass weight of said encapsulates.

AA. A composition according to any preceding claim, wherein said composition is in the form of a liquid composition, a granular composition, a single-compartment pouch, a multi-compartment pouch, a dissolvable sheet, a pastille or bead, a fibrous article, a tablet, a bar, a flake, a dryer sheet, or a mixture thereof.

BB. A composition according to any preceding claim, wherein said consumer product is a fabric and home care product, a beauty care product, or a mixture thereof, wherein if said consumer product is a fabric and home care product, preferably said fabric and home care product is selected from a laundry detergent composition, a fabric conditioning composition, a laundry and rinse additive, a fabric pre-treatment composition, a fabric refresher composition, or a mixture thereof; and wherein if said consumer product is a beauty care product, preferably said beauty care product is selected from a hair treatment product, a skin care product, a shave care product, a personal cleansing product, a deodorant and/or antiperspirant, or a mixture thereof.

CC. A method of treating a surface or an article, said method comprising (a) optionally washing, rinsing and/or drying said surface or article; (b) contacting said surface or article with a composition according to any preceding claim, optionally in the presence of water; and (c) optionally washing, rinsing and/or drying said surface or article, wherein said drying steps comprise active drying and/or passive drying.

Test Methods

It is understood that the test methods that are disclosed in the Test Methods Section of the present application should be used to determine the respective values of the parameters of the subject matter described and claimed herein.

(1) Extraction of Encapsulates from Finished Products.

Except where otherwise specified herein, the preferred method to isolate encapsulates from finished products is based on the fact that the density of most such encapsulates is different from that of water. The finished product is mixed with water in order to dilute and/or release the encapsulates. The diluted product suspension is centrifuged to speed up the separation of the encapsulates. Such encapsulates tend to float or sink in the diluted solution/dispersion of the finished product. Using a pipette or spatula, the top and bottom layers of this suspension are removed and undergo further rounds of dilution and centrifugation to separate and enrich the encapsulates. The encapsulates are observed using an optical microscope equipped with crossed-polarized filters or differential interference contrast (DIC), at total magnifications of 100× and 400×. The microscopic observations provide an initial indication of the presence, size, quality and aggregation of the encapsulates.

For extraction of encapsulates from a liquid fabric enhancer finished product conduct the following procedure:

1. Place three aliquots of approximately 20 ml of liquid fabric enhancer into three separate 50 ml centrifuge tubes and dilute each aliquot 1:1 with DI water (e.g. 20 ml fabric enhancer+20 ml DI water), mix each aliquot well and centrifuge each aliquot for 30 minutes at approximately 10000×g.
2. After centrifuging per Step 1, discard the bottom water layer (around 10 ml) in each 50 ml centrifuge tube then add 10 ml of DI water to each 50 ml centrifuge tube.
3. For each aliquot, repeat the process of centrifuging, removing the bottom water layer and then adding 10 ml of DI water to each 50 ml centrifuge tube two additional times.
4. Remove the top layer with a spatula or a pipette, and
5. Transfer this top layer into a 1.8 ml centrifuge tube and centrifuge for 5 minutes at approximately 20000×g.
6. Remove the top layer with a spatula and transfer into a new 1.8 ml centrifuge tube and add DI water until the tube is completely filled, then centrifuge for 5 minutes at approximately 20000×g.
7. Remove the bottom layer with a fine pipette and add DI water until tube is completely filled and centrifuge for 5 minutes at approximately 20000×g.
8. Repeat step 7 for an additional 5 times (6 times in total).

If both a top layer and a bottom layer of enriched encapsulates appear in the above described step 1, then, immediately move to step 3 (i.e., omit step 2) and proceed steps with steps 4 through 8. Once those steps have been completed, also remove the bottom layer from the 50 ml centrifuge tube from step 1, using a spatula or/and a pipette. Transfer the bottom layer into a 1.8 ml centrifuge tube and centrifuge 5 min at approximately 20000×g. Remove the bottom layer in a new tube and add DI water until the tube is completely filled then centrifuge for 5 minutes approximately 20000×g. Remove the top layer (water) and add DI water again until the tube is full. Repeat this another 5 times (6 times in total). Recombine the encapsulate enriched and isolated top and bottom layers back together.

If the fabric enhancer has a white color or is difficult to distinguish the encapsulate enriched layers add 4 drops of dye (such as Liquitint Blue JH 5% premix from Milliken & Company, Spartanburg, S.C., USA) into the centrifuge tube of step 1 and proceed with the isolation as described.

For extraction of encapsulates from solid finished products that disperse readily in water, mix 1 L of DI water with 20 g of the finished product (e.g. detergent foams, films, gels and granules; or water-soluble polymers; soap flakes and soap bars; and other readily water-soluble matrices such as salts, sugars, clays, and starches). When extracting encapsulates from finished products which do not disperse readily in water, such as waxes, dryer sheets, dryer bars, and greasy materials, it may be necessary to add detergents, agitation, and/or gently heat the product and diluent in order to release the encapsulates from the matrix. The use of organic solvents or drying out of the encapsulates should be avoided during the extraction steps as these actions may damage the encapsulates during this phase.

For extraction of encapsulates from liquid finished products which are not fabric softeners or fabric enhancers (e.g., liquid laundry detergents, liquid dish washing detergents, liquid hand soaps, lotions, shampoos, conditioners, and hair dyes), mix 20 ml of finished product with 20 ml of DI water. If necessary, NaCl (e.g., 100-200 g NaCl) can be added to the diluted suspension in order to increase the density of the solution and facilitate the encapsulates floating to the top layer. If the product has a white color which makes it difficult to distinguish the layers of encapsulates formed during centrifugation, a water-soluble dye can be added to the diluent to provide visual contrast.

The water and product mixture is subjected to sequential rounds of centrifugation, involving removal of the top and bottom layers, re-suspension of those layers in new diluent, followed by further centrifugation, isolation and re-suspension. Each round of centrifugation occurs in tubes of 1.5 to 50 ml in volume, using centrifugal forces of up to 20,000×g, for periods of 5 to 30 minutes. At least six rounds of centrifugation are typically needed to extract and clean sufficient encapsulates for testing. For example, the initial round of centrifugation may be conducted in 50 ml tubes spun at 10,000×g for 30 mins, followed by five more rounds of centrifugation where the material from the top and bottom layers is resuspended separately in fresh diluent in 1.8 ml tubes and spun at 20,000×g for 5 mins per round.

If encapsulates are observed microscopically in both the top and bottom layers, then the encapsulates from these two layers are recombined after the final centrifugation step, to create a single sample containing all the delivery encapsulates extracted from that product. The extracted encapsulates should be analyzed as soon as possible but may be stored as a suspension in DI water for up to 14 days before they are analyzed.

One skilled in the art will recognize that various other protocols may be constructed for the extraction and isolation of encapsulates from finished products and will recognize that such methods require validation via a comparison of the resulting measured values, as measured before and after the encapsulates' addition to and extraction from finished product.

(2) Encapsulate Size (Diameter):

A drop of the encapsulate suspension or finished product is placed onto a glass microscope slide and dried under ambient conditions for several minutes to remove the water and achieve a sparse, single layer of solitary encapsulates on the dry slide. Adjust the concentration of encapsulates in the suspension as needed to achieve a suitable encapsulate density on the slide. The slide is placed on a sample stage of an optical microscope equipped and examined at a total magnification of 100× or 400×. Images are captured and calibrated for the accurate measurement of encapsulate diameters. Three replicate slides are prepared and analyzed.

For encapsulate size measurement, at least 50 encapsulates on each slide are selected for measurement, in a manner which is unbiased by their size and so creates a representative sample of the distribution of encapsulate sizes present. This may be achieved by examining fields-of-view which are selected at random or according to a pre-defined grid pattern, and by measuring the diameter of all the encapsulates present in each field-of-view examined. Encapsulates which appear obviously non-spherical, deflated, leaking, or damaged are unsuitable for measurement, are excluded from the selection process and their diameters are not recorded. The diameter of each suitable encapsulate examined is measured using the microscope and the value is recorded. The recorded encapsulate diameter measurements are used to calculate the percentage of the encapsulates having an encapsulate size within the claimed size range(s), and also to calculate the median encapsulate size.

(3) Encapsulate Wall Thickness

The encapsulate wall thickness is measured in nanometers on 50 encapsulates using freeze-fracture cryo-scanning electron microscopy (FF cryoSEM), at magnifications of between 50,000× and 150,000×. Samples are prepared by flash freezing small volumes of a suspension of encapsulates or finished product. Flash freezing can be achieved by plunging into liquid ethane, or through the use of a device such as a High Pressure Freezer Model 706802 EM Pact, (Leica Microsystems, Wetzlar, Germany) Frozen samples are fractured while at −120° C., then cooled to below −160° C. and lightly sputter-coated with gold/palladium. These steps can be achieved using cryo preparation devices such as those from Gatan Inc., (Pleasanton, Calif., USA). The frozen, fractured and coated sample is then transferred at −170° C. or lower, to a suitable cryoSEM microscope, such as the Hitachi S-5200 SEM/STEM (Hitachi High Technologies, Tokyo, Japan). In the Hitachi S-5200, imaging is performed with 3.0 KV accelerating voltage and 5 µA-20 µA tip emission current.

Images are acquired of the fractured wall in cross-sectional view from 50 benefit delivery encapsulates selected in a random manner which is unbiased by their size, so as to create a representative sample of the distribution of encapsulate sizes present. The wall thickness of each of the 50 encapsulates is measured using the calibrated microscope software, by drawing a measurement line perpendicular to the outer surface of the encapsulate wall. The 50 independent wall thickness measurements are recorded and used to calculate the mean thickness, and the percentage of the encapsulates having a wall thickness within the claimed range.

(4) Benefit Agent Leakage

The amount of benefit agent leakage from the delivery encapsulates is determined according to the following method:

a.) Obtain two samples of the raw material slurry of encapsulates in such amounts so that 1 g of encapsulated perfume (e.g., 1 g perfume oil, not including the shell and/or partitioning modifier, if present) is present in each sample (or other amount as so indicated).

b.) Add one sample of the raw material slurry of encapsulates to a suitable amount of the product matrix (e.g., a liquid detergent product or an LFE product) in which the encapsulates will be employed to form 100 g total (e.g., 5 g slurry and 95 g product matrix) and label the mixture as Sample 1 Immediately use the second sample of raw material encapsulate slurry in Step d below, in its neat form without contacting product matrix, and label it as Sample 2.

c.) Age the encapsulate-containing product matrix (Sample 1) for one week at 35° C. (or other time and/or temperature, as so indicated) in a sealed, glass jar.

d.) Using filtration, recover the encapsulates from both samples. The encapsulates in Sample 1 (in product matrix) are recovered after the aging step. The encapsulates in Sample 2 (neat raw material slurry) are recovered at the same time that the aging step began for sample 1.

e.) Treat the recovered encapsulates with a solvent to extract the benefit agent materials from the encapsulates.

f.) Analyze the solvent containing the extracted benefit agent from each sample, via chromatography. Integrate the resultant benefit agent peak areas under the curve and sum these areas to determine the total quantity of benefit agent extracted from each sample.

g.) Determine the percentage of benefit agent leakage by calculating the difference in the values obtained for the total quantity of benefit agent extracted from Sample 2 minus Sample 1, expressed as a percentage of the total quantity of benefit agent extracted from Sample 2, as represented in the equation below:

$$\text{Percent of Benefit Agent Leakage} = \left(\frac{\text{Sample 2} - \text{Sample 1}}{\text{Sample 2}}\right) \times 100$$

(5) Viscosity

Viscosity of liquid finished product is measured using an AR 550 rheometer/viscometer from TA instruments (New Castle, Del., USA), using parallel steel plates of 40 mm diameter and a gap size of 500 µm. The high shear viscosity at 20 s$^{-1}$ and low shear viscosity at 0.05 s$^{-1}$ is obtained from a logarithmic shear rate sweep from 0.1 s$^{-1}$ to 25 s$^{-1}$ in 3 minutes time at 21° C.

(6) Perfume and Perfume Raw Materials (PRMs)

To determine the identity and to quantify the weight of perfume, perfume ingredients, or Perfume Raw Materials (PRMs), encapsulated within the delivery agent encapsulates, Gas Chromatography with Mass Spectroscopy/Flame Ionization Detector (GC-MS/FID) is employed. Suitable equipment includes: Agilent Technologies G1530A GC/FID; Hewlett Packer Mass Selective Device 5973; and 5%-Phenyl-methylpolysiloxane Column J&W DB-5 (30 m length×0.25 mm internal diameter×0.25 µm film thickness). Approximately 3 g of the finished product or suspension of delivery encapsulates, is weighed and the weight recorded, then the sample is diluted with 30 mL of DI water and filtered through a 5.0 µm pore size nitrocellulose filter membrane. Material captured on the filter is solubilized in 5 mL of ISTD solution (25.0 mg/L tetradecane in anhydrous alcohol) and heated at 60° C. for 30 minutes. The cooled solution is filtered through 0.45 µm pore size PTFE syringe filter and analyzed via GC-MS/FID. Three known perfume oils are used as comparison reference standards. Data Analysis involves summing the total area counts minus the ISTD area counts and calculating an average Response Factor (RF) for the 3 standard perfumes. Then the Response Factor and total area counts for the product encapsulated perfumes are used along with the weight of the sample, to determine the total weight percent for each PRM in the encapsulated perfume. PRMs are identified from the mass spectrometry peaks.

(7) Test Method for Determining logP

The value of the log of the Octanol/Water Partition Coefficient (logP) is computed for each PRM in the perfume mixture being tested. The logP of an individual PRM is calculated using the Consensus logP Computational Model, version 14.02 (Linux) available from Advanced Chemistry Development Inc. (ACD/Labs) (Toronto, Canada) to provide the unitless logP value. The ACD/Labs' Consensus logP Computational Model is part of the ACD/Labs model suite.

(8) Volume Weighted Median Encapsulate Size

Encapsulate size is measured using an Accusizer 780 A, made by Encapsulate Sizing Systems, Santa Barbara Calif. The instrument is calibrated from 0 to 300µ using Duke encapsulate size standards. Samples for encapsulate size evaluation are prepared by diluting about 1 g emulsion, if the volume weighted median encapsulate size of the emulsion is to be determined, or 1 g of capsule slurry, if the finished capsule volume weighted median encapsulate size is to be determined, in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The Accusizer will dilute the test sample until 9200 counts/second and initiate the evaluation. After 2 minutes of testing the Accusizer will display the results, including volume-weighted median size.

The broadness index can be calculated by determining the encapsulate size at which 95% of the cumulative encapsulate volume is exceeded (95% size), the encapsulate size at which 5% of the cumulative encapsulate volume is exceeded (5% size), and the median volume-weighted encapsulate size (50% size-50% of the encapsulate volume both above and below this size). Broadness Index (5)=((95% size)−(5% size)/50% size).

EXAMPLES

While particular embodiments of the present subject matter have been illustrated and described, it would be obvious to those skilled in the art that various other changes and modifications can be made without departing from the spirit and scope of the invention. It is therefore intended to cover in the appended claims all such changes and modifications that are within the scope of this disclosure.

Encapsulate Preparation—Procedure 1:

A first oil phase, consisting of 37.50 g of perfume oil, 0.22 g tert-butylamino ethyl methacrylate, 0.22 g 2-carboxyethyl acrylate, and 18.00 g multi-functional acrylate monomer or oligomer is prepared under mixing for 30 minutes at room temperature.

A second oil phase consisting of 112.50 g of the perfume oil, 37.50 g isopropyl myristate, 1.00 g 2,2'-azobis(2-methylbutyronitrile), and 0.80 g 4,4'-azobis[4-cyanovaleric acid] is added to a jacketed steel reactor. The reactor is held at 35° C. and the oil solution is mixed at 600 RPMs, under a nitrogen blanket. The solution is heated to 70° C. and held at 70° C. for 45 minutes, before cooling to 50° C. At 50° C., the first oil phase is added to the reactor and the combined oils are mixed for 10 minutes at 50° C.

A water phase, containing 70.03 g Selvol 540 PVA (Sekisui Specialty Chemicals, Dallas, Tex.) at 5% solids, 221.06 g water, 1.10 g 4,4'-azobis[4-cyanovaleric acid], and 1.20 g NaOH at 21.5% is prepared and mixed until fully dissolved. After the oil phases are pre-reacted together for 10 minutes at 50° C., mixing is ceased, and the water phase mixture is added to the oil phases. High shear agitation is applied to produce an emulsion with the desired size characteristics. The temperature is increased to 75° C., held at 75° C. for 4 hours, increased to 95° C., and held at 95° C. for 6 hours. The batch is allowed to cool to room temperature.

Examples 1-11

Following the encapsulate preparation procedure 1, the multifunctional monomer used is tris-(2-hydroxyethyl) isocyanurate triacrylate. The resultant encapsulates are of varying median encapsulate size, as depicted in Table 1.

Comparative Example 12

Following the encapsulate preparation procedure 1, the multifunctional monomer is a commercial hexafunctional aromatic urethane acrylate CN975 (Sartomer, Exton, Pa.).

Comparative Examples 13

Following the encapsulate preparation procedure 1, the multifunctional monomer is an aliphatic urethane acrylate Ebecryl 8602 (Allnex, Frankfurt, Germany).

Comparative Example 14

Following the encapsulate preparation procedure 1, the multifunctional monomer is a hexafunctional aromatic urethane acrylate Ebecryl 220 (Allnex, Frankfurt, Germany).

Comparative Example 15

Following the encapsulate preparation procedure 1, the multifunctional monomer is an aliphatic urethane acrylate Ebecryl 8701 (Allnex, Frankfurt, Germany).

Comparative Example 16

Following the encapsulate preparation procedure 1, the multifunctional monomer is an aliphatic urethane acrylate Ebecryl 8301R (Allnex, Frankfurt, Germany).

Example 17

Following the encapsulate preparation procedure 1, the multifunctional monomer is 90% by weight tris (2-hydroxyethyl) isocyanurate triacrylate and 10% by weight 2-trifunctional acrylate SR517HP (Sartomer, Exton, Pa.).

Comparative Example 18

Following the encapsulate preparation procedure, the multifunctional monomer is an aliphatic urethane acrylate Ebecryl 8415 (Allnex, Frankfurt, Germany).

Comparative Example 19

Following the encapsulate preparation procedure 1, the multifunctional monomer is an aliphatic urethane acrylate Ebecryl 2221 (Allnex, Frankfurt, Germany).

Examples 20-24

An encapsulate is prepared following encapsulate preparation procedure 1, and the multifunctional monomer used is tris-(2-hydroxyethyl) isocyanurate triacrylate, kept at a constant amount, to which is added 20% by weight of the two monomers as indicated in Table 1.

Comparative Examples 25-26

Following the encapsulate preparation procedure 1, the multifunctional monomer is a commercial hexafunctional aromatic urethane acrylate CN975 (Sartomer, Exton, Pa.). Table 1 contains data for examples produced according to procedure 1.

To obtain the leakage data in Table 1, the encapsulates are tested in a liquid detergent product matrix. The encapsulates are provided in a suitable amount to provide 1 g of encapsulated perfume. The resulting liquid detergent product has the following formulation as provided in Table A.

TABLE A

|  | wt % Active |
|---|---|
| Alkyl ether sulfate (AES) | 4.0 |
| Dodecyl benzene sulphonic acid (HLAS) | 9.2 |
| Ethoxylated alcohol | 4.1 |
| Amine oxide | 0.5 |
| Fatty acid | 1.7 |
| Citric acid | 2.8 |

TABLE A-continued

| | wt % Active |
|---|---|
| Sodium diethylene triamine penta methylene phosphonic acid | 0.5 |
| Calcium chloride | 0.01 |
| Sodium formate | 0.03 |
| Ethoxysulfated hexamethylene diamine quaternized | 0.7 |
| Co-polymer of polyethylene glycol and vinyl acetate | 1.3 |
| Optical Brightener 49 | 0.05 |
| Perfume oil in microcapsule | 1.0 |
| 1,2-benzisothiazolin-3-one and 2-methyl-4-isothiazolin-3-one | 0.005 |
| Ethanol | 0.4 |
| 1,2-propanediol | 1.3 |
| Sodium cumene sulphonate | 1.7 |
| Mono ethanol amine | 0.2 |
| NaOH | 3.1 |
| Structurant (hydrogenated castor oil) | 0.3 |
| Silicone emulsion | 0.0025 |
| Dye | 0.005 |
| water | Balance |

Encapsulate Preparation—Procedure 2:

A first oil phase, consisting of 44.50 g of perfume oil, 0.74 g tert-butylamino ethyl methacrylate, 0.74 g 2-carboxyethyl acrylate, and 41.30 g multi-functional acrylate monomer or oligomer is prepared under mixing for 30 minutes at room temperature.

A second oil phase consisting of 142.67 g of perfume oil, 1.29 g 2,2'-azobis(2-methylbutyronitrile), and 0.98 g 4,4'-azobis[4-cyanovaleric acid] is added to a jacketed steel reactor. The reactor is held at 35° C. and the oil solution is mixed at 600 RPMs under a nitrogen blanket. The solution is heated to 70° C. and held at 70° C. for 45 minutes, before cooling to 50° C. At 50° C., the first oil phase is added to the reactor and the combined oils are mixed for another 10 minutes at 50° C.

A water phase, containing 70.03 g Selvol 540 PVA (Sekisui Specialty Chemicals, Dallas, Tex.) at 5% solids, 221.06 g water, 0.42 g 4,4'-azobis[4-cyanovaleric acid], and 0.46 g 21.5% NaOH, is prepared and mixed until fully dissolved. After the oil phases are pre-reacted together for 10 minutes at 50° C., mixing is ceased, and the water phase mixture is added to the mixed oil phases. High shear

TABLE 1

| Example # | Monomer/Oligomer | Monomer/Oligomer Description | Core (component 1/component 2 = wt. ratio) | Median Encap. Size (μm) | Leakage (%) |
|---|---|---|---|---|---|
| Example 1 | SR368 | tris (2-hydroxyethyl) isocyanurate triacrylate | perfume oil/IPM = 80/20 | 18.06 | 15.3 |
| Example 2 | SR368 | tris (2-hydroxyethyl) isocyanurate triacrylate | perfume oil/IPM/parafol 22 = 80/10/10 | 15.88 | 19.4 |
| Example 3 | SR368 | tris (2-hydroxyethyl) isocyanurate triacrylate | perfume oil/dodecanophenone = 80/20 | 30.34 | 17.6 |
| Example 4 | SR368 | tris (2-hydroxyethyl) isocyanurate triacrylate | perfume oil/lauryl laurate = 80/20 | 33.11 | 17.3 |
| Example 5 | SR368 | tris (2-hydroxyethyl) isocyanurate triacrylate | perfume oil/methyl behenate = 80/20 | 19.15 | 24.1 |
| Example 6 | SR368 | tris (2-hydroxyethyl) isocyanurate triacrylate | perfume oil/methyl laurate = 80/20 | 37.49 | 14.1 |
| Example 7 | SR368 | tris (2-hydroxyethyl) isocyanurate triacrylate | perfume oil/ methyl palmitate = 80/20 | 37.49 | 15.7 |
| Example 8 | SR368 | tris (2-hydroxyethyl) isocyanurate triacrylate | perfume oil/methyl stearate = 80/20 | 33.52 | 10.5 |
| Example 9 | SR368 | tris (2-hydroxyethyl) isocyanurate triacrylate | perfume oil/methyl stearate = 80/20 | 18.48 | 20.5 |
| Example 10 | SR368 | tris (2-hydroxyethyl) isocyanurate triacrylate | perfume oil/parafol 18 = 80/20 | 18.48 | 18.4 |
| Example 11 | SR368 | tris (2-hydroxyethyl) isocyanurate triacrylate | perfume oil/parafol 22 = 80/20 | 18.70 | 15.0 |
| Comparative example 12 | CN975 | aromatic urethane acrylate | perfume oil/IPM = 80/20 | 16.64 | 54.3 |
| Comparative example 13 | EBECRYL 8602 | aliphatic urethane acrylate | perfume oil/IPM = 80/20 | 17.64 | 55.5 |
| Comparative example 14 | EBECRYL 220 | aromatic urethane acrylate | perfume oil/IPM = 80/20 | 19.15 | 26.6 |
| Comparative example 15 | EBECRYL 8701 | aliphatic urethane acrylate | perfume oil/IPM = 80/20 | 18.27 | 46.9 |
| Comparative example 16 | EBECRYL 8301R | aliphatic urethane acrylate | perfume oil/IPM = 80/20 | 18.06 | 95.1 |
| Example 17 | SR368 with 10% SR517HP | tris (2-hydroxyethyl) isocyanurate triacrylate with trifunctional coagent | perfume oil/IPM = 80/20 | 17.85 | 40.2 |
| Comparative example 18 | EBECRYL 8415 | aliphatic urethane acrylate | perfume oil/IPM = 80/20 | 17.23 | 76.6 |
| Comparative example 19 | EBECRYL 2221 | aromatic Urethane acrylate | perfume oil/IPM = 80/20 | 18.06 | 67.5 |
| Example 20 | SR368 with 20% EB8415 | tris (2-hydroxyethyl) isocyanurate triacrylate with aliphatic urethane acrylate | perfume oil/IPM = 80/20 | 18.92 | 20.8 |
| Example 21 | SR368 with 20% EB2221 | tris (2-hydroxyethyl) isocyanurate triacrylate with aromatic Urethane acrylate | perfume oil/IPM = 80/20 | 17.43 | 33.3 |
| Example 22 | SR368 with 20% EB8701 | tris (2-hydroxyethyl) isocyanurate triacrylate with aliphatic urethane acrylate | perfume oil/IPM = 80/20 | 18.27 | 26.7 |
| Example 23 | SR368 with 20% EB220 | tris (2-hydroxyethyl) isocyanurate triacrylate with aromatic Urethane acrylate | perfume oil/IPM = 80/20 | 18.06 | 14.4 |
| Example 24 | SR368 with 20% EB8602 | tris (2-hydroxyethyl) isocyanurate triacrylate with aliphatic urethane acrylate | perfume oil/IPM = 80/20 | 17.85 | 21.5 |
| Comparative example 25 | CN975 | aromatic urethane acrylate | perfume oil/parafol 18 = 80/20 | 18.06 | 39.6 |
| Comparative example 26 | CN975 | aromatic urethane acrylate | perfume oil/parafol 22 = 80/20 | 17.03 | 39.6 | agitation is applied to produce an emulsion with the desired size characteristics. The temperature is increased to 75° C., held at 75° C. for 4 hours, increased to 95° C., and held at 95° C. for 6 hours. The batch is allowed to cool to room temperature.

Example 27

Following the encapsulate preparation procedure 2, the multifunctional monomer used is tris-(2-hydroxyethyl) isocyanurate triacrylate.

Comparative Example 28

Following the encapsulate preparation procedure 2, the multifunctional monomer used is a blend by weight of 45% tris-(2-hydroxyethyl) isocyanurate triacrylate and 55% ethylene glycol dimethacrylate.

Comparative Example 29

Following the encapsulate preparation procedure 2, the multifunctional monomer used is a blend by weight of 45% tris-(2-hydroxyethyl) isocyanurate triacrylate and 55% pentaerythritol tetraacrylate.

Comparative Example 30

Following the encapsulate preparation procedure 2, the multifunctional monomer used is a blend by weight of 60% tris-(2-hydroxyethyl) isocyanurate triacrylate and 40% tricyclodecane dimethanol diacrylate.

Comparative Example 31

Following the encapsulate preparation procedure 2, the multifunctional monomer used is a blend by weight of 70% trimethylol propane triacrylate and 30% tris-(2-hydroxyethyl) isocyanate triacrylate.

Comparative Example 32

Following the encapsulate preparation procedure 2, the multifunctional monomer used is pentaerythritol tetraacrylate.

Table 2 contains data for examples produced according to procedure 2. To obtain the leakage data in Table 2, the encapsulates are tested in a liquid detergent product matrix. The encapsulates are provided in a suitable amount to provide 1 g of encapsulated perfume. The resulting liquid detergent product has the following formulation as provided in Table A, above.

Example 33

Production of Spray Dried Encapsulates 1200 g of perfume encapsulate slurry, containing one or more of the variants of encapsulates disclosed in the present specification, is mixed together with 700 g of water for 10 minutes using an IKA Eurostar mixer with R1382 attachment at a speed of 180 rpm. The mixture is then transferred over to a feeding vessel to be spray dried in a 1.2 m diameter Niro Production Minor. The slurry is fed into the tower using a Watson-Marlow 504 U peristaltic pump and atomized using a 100 mm diameter rotary atomizer run at 18000 rpm, with co-current air flow for drying. The slurry is dried using an inlet temperature of 200° C. and outlet temperature of 95° C. to form a fine powder. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 34

Encapsulate Performance in a Liquid Fabric Enhancer Product

To test the performance benefits of the encapsulates of the present disclosure, liquid fabric enchancer ("LFE") products are made. The LFE products contain approximately 0.33% of perfume oil added via encapsulates. The LFE products have the formulation as provided in Table B.

TABLE B

|  | wt % Active |
|---|---|
| Diester Quat | 8 |
| Formic Acid | 0.05 |
| Hydrochloric acid | 0.01 |
| 1,2-benzisothiazolin-3-one | 0.0045 |
| Silicone | 0.01 |
| Sodium hydroxyethane diphosphonic acid | 0.01 |
| Perfume oil in microcapsule | 0.33 |
| Structurant | 0.11 |
| Water and minors | Balance |

In the present test, two type of encapsulates are tested: encapsulates made in accordance with Example 2 of USPA

TABLE 2

| Example # | Monomer/Oligomer | Monomer/Oligomer Description | Core | Median Encap. Size (μm) | Leakage (%) |
|---|---|---|---|---|---|
| Example 27 | SR368 | tris (2-hydroxyethyl) isocyanurate triacrylate | 100% perfume oil | 21.92 | 20.0 |
| Comparative example 28 | SR368/SR206 = 45/55 | tris (2-hydroxyethyl) isocyanurate triacrylate with ethylene glycol dimethacrylate | 100% perfume oil | 19.15 | 78.0 |
| Comparative example 29 | SR368/SR295 = 45/55 | tris (2-hydroxyethyl) isocyanurate triacrylate with pentaerythritol tetraacrylate | 100% perfume oil | 18.65 | 74.9 |
| Comparative example 30 | SR368/SR833S = 60/40 | tris (2-hydroxyethyl) isocyanurate triacrylate with TRICYCLODECANE DIMETHANOL DIACRYLATE | 100% perfume oil | 20.60 | 79.6 |
| Comparative example 31 | SR368D | 70/30 = SR351 (trimethylolpropane triacrylate)/SR368 | 100% perfume oil | 17.75 | 83.8 |
| Comparative example 32 | SR295 | pentaerythritol tetraacrylate | 100% perfume oil | 17.53 | 50.2 |

2008/0305982 (as a comparative example), and encapsulates made in accordance with Example 1 of the present application (as an inventive example).

Each wash test contains a load of ballast and tracers. The ballast portion of the load is 3 kg and contains: 600 g Polyester; 600 g Polycotton; 600 g Muslin (flat) cotton; 600 g Kitted cotton; and 600 g Terry towels. The ballast loads are preconditioned according to the following conditions: 2×70 g Ariel Sensitive, 95° C. wash+2×nil powder, short cotton wash @ 95° C. After each wash test, the ballast load is rewashed according to the following conditions: 2×70 g Ariel Sensitive, 95° C. wash+2×nil powder, short cotton wash @ 95° C.

For each wash test, six terry tracers (Maes Textiel) are added to the load. The tracers are preconditioned according to the following conditions: 2×70 g Ariel Sensitive, 95° C. wash+2×nil powder, short cotton wash @ 95° C. Tracers are not re-used.

Before each test, the washing machine is "boil washed" (short cotton wash cycle @ 95° C.). The test conditions are as follows. The machine used is a Miele Novotronic W526 automatic washing machine The load is put into the washing machine. A dosage of 50 g Ariel Sensitive powder is added to the appropriate dispenser. A dosage of 35 mL of the LFE product to be tested is added to the appropriate dispenser. The load is treated with a wash cycle according to the following conditions: short cotton cycle wash at 60° C., 1200 rpm spin speed.

After treatment, the terry tracers are evaluated by perfumers and graded on the Primavera scale. The primavera scale is an odor perfume intensity scale based on a scale from 0-100, where 10 point difference is consumer noticeable. On the scale, 0=no perfume odor, 25=slight perfume odor, 50=moderate perfume odor, 75=strong perfume odor and 100=extremely strong perfume odor.

The tracers are evaluated at various "touch points"—while wet (wet fabric odor, or "WFO") and after one day of line-drying (no rubbing of the fabric) (dry fabric odor, or "DFO"). The encapsulates are also tested for perfume leakage in the LFE product after one week of storage at 35° C. Results are shown in Table 3.

To test for leakage, the encapsulates are provided to a liquid detergent product according to Table A above, and tested according to the test method provided herein.

TABLE 3

| Ex. | Encapsulate Type | Delta on WFO | Delta on DFO | Leakage (1 wk at 35° C.) |
|---|---|---|---|---|
| A (comp) | Encapsulates made in accordance with Example 2 of USPA 2008/0305982 A1 | ref | ref | 5.6% |
| B (inv) | Encapsulates made in accordance with Example 1 of the present application | +10 | 0 | 2.1% |

The data shows that on wet fabrics, the odor performance of the encapsulates according to the present application is improved when compared to the encapsulates of Example 2 of USPA 2008/0305982 A1, without loss of performance on dry fabrics. Example B also shows relatively less leakage than Example A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a consumer product adjunct material and encapsulates having a volume weighted median encapsulate size from about 0.5 microns to about 100 microns, said encapsulates comprising a core and a shell, said shell encapsulating said core, a) said shell comprising a poly(meth)acrylate polymer comprising a reaction product of at least one monomer or oligomer thereof, i. the monomer comprising a structure according to formula I

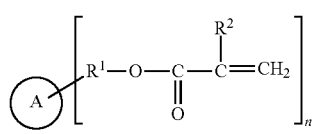

wherein $R^1$ is selected from $C_1$ to $C_8$ alkyl;

wherein $R^2$ is hydrogen or methyl;

wherein n is 3;

wherein A is a ring structure selected from:

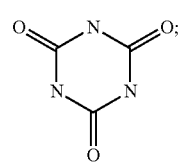

b. said core comprising a benefit agent, wherein said benefit agent is perfume raw materials; said core further comprising, based on total core weight, from greater than 0% to about 80%, of a partitioning modifier, said composition being a consumer product.

2. The composition according to claim 1, wherein said poly(meth)acrylate polymer of the shell comprises a reaction product of at least three monomers or oligomers thereof comprising a first monomer, a second monomer, and a third monomer,
   a. the first monomer comprising the structure according to formula I,
   b. the second monomer comprising a basic (meth)acrylate monomer,
   c. the third monomer comprising an acidic (meth)acrylate monomer.

3. The composition according to claim 2, wherein the basic
   (meth)acrylate monomer or oligomer thereof comprises less than 1% by weight of the encapsulate, and
   the acidic (meth)acrylate monomer or oligomer thereof comprises less than 1% by weight of the encapsulate.

4. The composition according to claim 1, wherein the volume weighted median encapsulate size is from 25 microns to 60 microns.

5. The composition according to claim 1, wherein in formula I, $R^1$ is selected from $C_2$ to $C_5$ alkyl.

6. The composition according to claim 1, wherein the monomer according to formula I is selected from

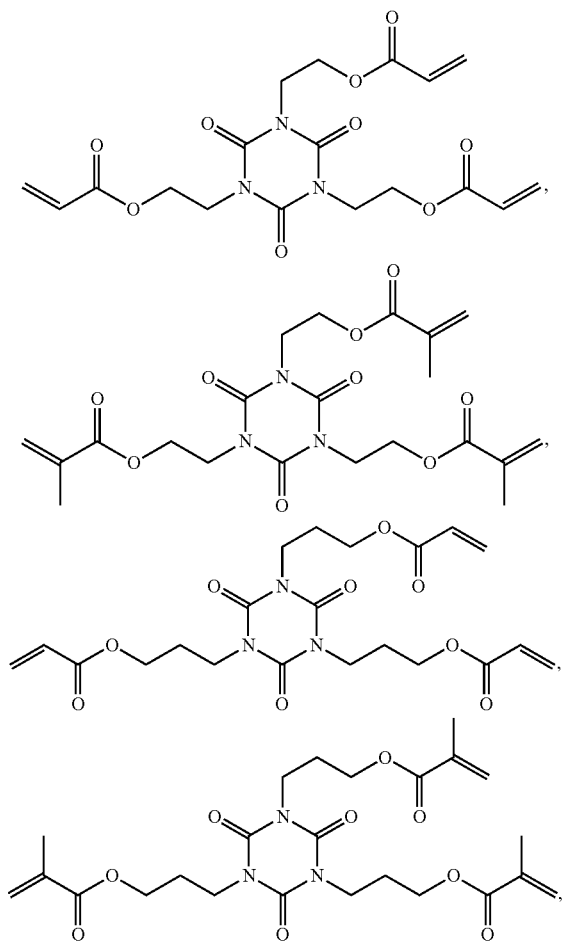

-continued

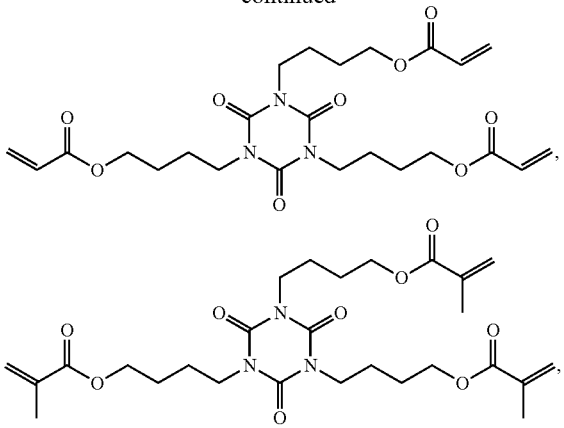

or an oligomer of any such monomer.

7. The composition according claim 1, wherein said partitioning modifier comprising a modifier selected from the group consisting of vegetable oil, modified vegetable oil, mono-, di-, and tri-esters of $C_4$-$C_{24}$ fatty acids, propan-2-yl tetradecanoate, dodecanophenone, lauryl laurate, methyl behenate, methyl laurate, methyl palmitate, methyl stearate, and mixtures thereof.

8. The composition according to claim 7, wherein said partitioning modifier comprises propan-2-yl tetradecanoate.

9. The composition according to claim 1, wherein the encapsulate, based on total encapsulate weight, comprises from about 0.5% to about 40%, of an emulsifier.

10. The composition according to claim 9, wherein said emulsifier is selected from the group consisting of polyvinyl alcohol, carboxylated or partially hydrolyzed polyvinyl alcohol, methyl cellulose, hydroxyethylcellulose, carboxymethylcellulose, methylhydroxypropylcellulose, salts or esters of stearic acid, lecithin, organosulphonic acid, 2-acrylamido-2-alkylsulphonic acid, styrene sulphonic acid, polyvinylpyrrolidone, copolymers of N-vinylpyrrolidone, polyacrylic acid, polymethacrylic acid, copolymers of acrylic acid and methacrylic acid, water-soluble surfactant polymers which lower the surface tension of water, and mixtures thereof.

11. The composition according to claim 10, wherein said emulsifier comprises polyvinyl alcohol, wherein said polyvinyl alcohol has at least one of the following properties:
   (i) a hydrolysis degree from about 55% to about 99%; and/or
   (ii) a viscosity of from about 40 cps to about 80 cps in 4% water solution at 20° C.; and/or
   (iii) a degree of polymerization of from about 1500 to about 2500; and/or
   (iv) a weight average molecular weight of from about 130,000 to about 204,000 Daltons; and/or
   (v) a number average molecular weight of from about 65,000 to about 110,000 Daltons.

12. The composition according to claim 1, wherein the encapsulate comprises a coating on said shell.

13. The composition according to claim 1, wherein said consumer product adjunct material is selected from the group consisting of: surfactants, conditioning actives, deposition aids, rheology modifiers or structurants, bleach systems, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, additional perfumes and perfume delivery systems, structure elasticizing agents, carriers, hydrotropes, processing aids, structurants, anti-agglomeration agents, coatings, formaldehyde scavengers, pigments, and mixtures thereof.

14. A composition according to claim 1, wherein said composition is in the form of a liquid composition, a granular composition, a single-compartment pouch, a multi-compartment pouch, a dissolvable sheet, a pastille or bead, a fibrous article, a tablet, a bar, a flake, a dryer sheet, or a mixture thereof.

15. A composition according to claim 1, wherein said consumer product is a fabric and home care product, a beauty care product, or a mixture thereof.

16. A composition comprising a consumer product adjunct material and encapsulates, said encapsulates having a volume weighted median encapsulate size from about 0.5 microns to about 100 microns, said encapsulates comprising a core and a shell, said shell encapsulating said core,
   a) said shell comprising a poly(meth)acrylate polymer comprising a reaction product of at least a first monomer, a second monomer, and a third monomer, or oligomers thereof,
      i. the first monomer comprising the structure according to formula I,

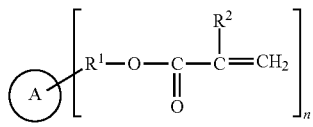

wherein $R^1$ is selected from $C_1$ to $C_8$ alkyl;
wherein $R^2$ is hydrogen or methyl;
wherein n is 3;
wherein A is a ring structure selected from:

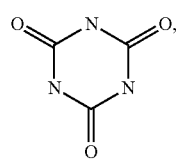

with the proviso that said shell is free of polymers formed from monofunctional ethylenically unsaturated monomers;
      ii. the second monomer comprising a basic (meth)acrylate monomer,
      iii. the third monomer comprising an acidic (meth)acrylate monomer; and
   b) said core comprising a benefit agent, said benefit agent comprising perfume raw materials;
wherein said composition is a consumer product.

17. The composition according to claim 16,
wherein the basic (meth)acrylate monomer or oligomer comprises an aminoalkyl acrylate or aminoalkyl methacrylate, wherein the alkyl moieties are from one to twelve carbons; and/or wherein the acidic (meth)acrylate monomer or oligomer comprises a carboxy-substituted acrylate or methacrylate monomer.

18. The composition according to claim 17,
wherein the basic (meth)acrylate monomer is selected from the group consisting of ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate, diethylamino acrylate, diethylamino methacrylate, diethylaminoethyl acrylate diethylaminoethyl methacrylate, dimethylaminoethyl acrylate and dimethylaminoethyl methacrylate; and/or wherein the acidic (meth)acrylate monomer is selected from the group consisting of 2-carboxyethyl acrylate, 2-carboxyethyl methacrylate, 2-carboxypropyl acrylate, 2-carboxypropyl methacrylate, carboxyoctyl acrylate, carboxyoctyl methacrylate, 2-acryloyloxybenzoic acid, 3-acryloyloxybenzoic acid, 4-acryloyloxybenzoic acid, 2-methacryloyloxybenzoic acid, 3-methacryloyloxybenzoic acid, and 4-methacryloyloxybenzoic acid, 4-acryloyloxyphenylacetic acid, and 4-methacryloyloxyphenylacetic acid.

19. The composition according to claim 16, wherein the basic
   (meth)acrylate monomer or oligomer thereof comprises less than 1% by weight of the encapsulate, and
   the acidic (meth)acrylate monomer or oligomer thereof comprises less than 1% by weight of the encapsulate.

20. The composition according to claim 1, wherein the monomer according to formula I is

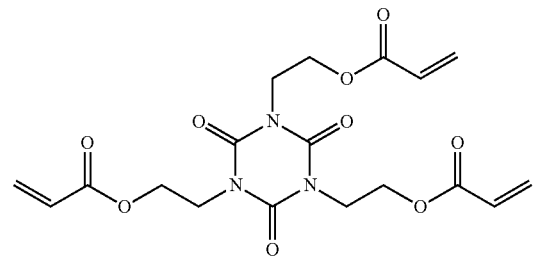 [SMILES: C=CC(=O)OCCn1c(=O)n(CCOC(=O)C=C)c(=O)n(CCOC(=O)C=C)c1=O]

and/or an oligomer thereof.

21. The composition according to claim 16, wherein the monomer according to formula I is

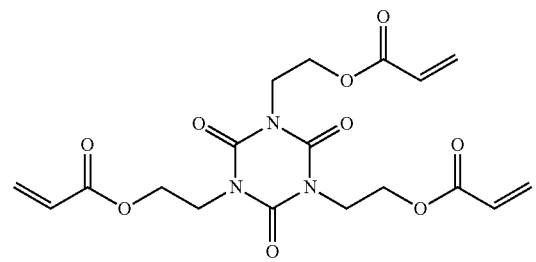 [SMILES: C=CC(=O)OCCn1c(=O)n(CCOC(=O)C=C)c(=O)n(CCOC(=O)C=C)c1=O]

and/or an oligomer thereof.

* * * * *